US008987221B2

(12) United States Patent
Zhu et al.

(10) Patent No.: US 8,987,221 B2
(45) Date of Patent: Mar. 24, 2015

(54) POTENTIATION OF AUTOIMMUNE AND INFLAMMATORY DISEASE TREATMENTS BY IMMUNE REGULATORY OLIGONUCLEOTIDE (IRO) ANTAGONISTS OF TLR7 AND TLR9

(75) Inventors: Fu-Gang Zhu, Bedford, MA (US); Ekambar Kandimalla, Southboro, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 662 days.

(21) Appl. No.: 12/791,636

(22) Filed: Jun. 1, 2010

(65) Prior Publication Data

US 2011/0171209 A1 Jul. 14, 2011

Related U.S. Application Data

(60) Provisional application No. 61/182,928, filed on Jun. 1, 2009.

(51) Int. Cl.
*A61K 48/00* (2006.01)
*C12N 15/11* (2006.01)
*A61K 31/7088* (2006.01)
*A61K 38/17* (2006.01)
*A61K 45/06* (2006.01)
*C12N 15/117* (2010.01)

(52) U.S. Cl.
CPC .......... *C12N 15/117* (2013.01); *A61K 31/7088* (2013.01); *A61K 38/1793* (2013.01); *A61K 45/06* (2013.01); *A61K 2300/00* (2013.01); *C12N 2310/17* (2013.01); *C12N 2310/3183* (2013.01); *C12N 2310/319* (2013.01); *C12N 2310/321* (2013.01); *C12N 2310/332* (2013.01); *C12N 2310/336* (2013.01); *C12N 2310/3521* (2013.01); *C12N 2310/51* (2013.01); *C12N 2320/31* (2013.01)
USPC ........................................... 514/44; 435/23.1

(58) Field of Classification Search
None
See application file for complete search history.

(56) References Cited

U.S. PATENT DOCUMENTS

| | | | | |
|---|---|---|---|---|
| 5,527,899 | A | * | 6/1996 | Froehler ........................ 536/25.3 |
| 6,096,722 | A | * | 8/2000 | Bennett et al. ................ 514/44 A |
| 2004/0097719 | A1 | | 5/2004 | Agrawal et al. |
| 2009/0081198 | A1* | | 3/2009 | Kandimalla et al. ........ 424/130.1 |
| 2009/0087388 | A1* | | 4/2009 | Kandimalla et al. ............. 424/45 |

FOREIGN PATENT DOCUMENTS

| | | |
|---|---|---|
| EP | 2 154 144 | 2/2010 |
| WO | WO 2005/072290 A2 | 8/2005 |
| WO | WO 2007/038720 A2 | 4/2007 |

OTHER PUBLICATIONS

McInnes et al. N Engl J Med 2011;365:2205-19.*
Hughes et al. BioDrugs 2001; 15(6):379-393.*
Iribarren et al. PNAS vol. 87, pp. 7747-7751, Oct. 1990.*
Aurisicchio et al., "Treatment of mammary carcinomas in HER-2 transgenic mice through combination of genetic vaccine and an agonist of toll-like receptor 9", Clinical Cancer Research, vol. 15, No. 5, Feb. 17, 2009, pp. 1575-1584, XP55014631.
Wang et al., "Immunomodulatory oligonucleotides as novel therapy for breast cancer: pharmacokinetics, in vitro and in vivo anticancer activity, and potentiation of antibody therapy", Molecular Cancer Therapeutics, vol. 5, No. 8, Aug. 1, 2006, pp. 2106-2114, XP55014635.
Damiano et al., "TLR9 agonist acts by different mechanisms synergizing with bevacizumab in sensitive and cetuximab-resistant colon cancer xenografts", Proceedings of the National Academy of Sciences, vol. 104, No. 30, Jul. 24, 2007, pp. 12468-12473, XP55014634.
Agrawal et al., "Medicinal chemistry and therapeutic potential of CpG DNA", Trends in Molecular Medicine, Elsevier Current Trends, GB, vol. 8, No. 3, Mar. 1, 2002, pp. 114-121, XP009073678.
Loos et al., "TLR ligands and cytokines induce CXCR3 ligands in endothelial cells: enhanced CXCL9 in autoimmune arthritis", Laboratory Investigation, vol. 86, No. 9, Sep. 1, 2006, pp. 902-916, XP55014656.
Korzenik et al., "Evolving knowledge and therapy of inflammatory bowel disease", Nature Reviews Drug Discovery, vol. 5, No. 3, Mar. 1, 2006, pp. 197-209, XP55014668.
Idera Pharmaceuticals Internet Article, "Idera Pharmaceuticals to Present Preclinical Data on its Agonists of Toll-Like Receptors at AACR 2009 Annual Meeting", Apr. 15, 2009, XP002666052.
Idera Pharmaceuticals Internet Article, Idera Pharmaceuticals: "Idera Pharmaceuticals Announces Presentation of Preclinical Data on IMO-3100, a Lead TLR Antagonist Drug Candidate for Autoimmune Diseases, during American Association of Immunologists Annual Meeting", May 11, 2009, XP00266053.
Zhu et al., "Studies of combination of IMO-3100, an antagonist of TLR7 and TLR9, and etanercept, a TNF-alpha inhibitor, in a mouse model of collagen-induced arthritis (CIA)", Annual Scientific Meeting of the American College of Rheumatology and Association of Rheumatology Health Professionals, Oct. 19, 2009, XP55014802.
Idera Pharmaceuticals: "Idera Pharmaceuticals Presents Preclinical Data at ACR/ARHP 2009 Annual Meeting on IMO-3100, a Toll-Like Receptor Antagonist in Combination with Enbrel® in Arthritis Model", Oct. 19, 2009, XP002666054.

* cited by examiner

*Primary Examiner* — Oluwatosin Ogunbiyi
(74) *Attorney, Agent, or Firm* — Elmore Patent Law Group, P.C.; Joseph C. Zucchero; Carolyn S. Elmore, Esq.

(57) ABSTRACT

The invention provides the use of immune regulatory oligonucleotides (IRO) as antagonist of TLRs and potentiators of anti-inflammatory agents that inhibit TNF for the prevention and treatment of inflammatory and autoimmune diseases.

11 Claims, 7 Drawing Sheets

SEQUENCE LISTING

```
<160> NUMBER OF SEQ ID NOS: 99

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
ctatctgacg ttctctgt                                                    18

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 2
ctatctgtcg ttctctgt                                                    18

<210> SEQ ID NO 3
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: 7-deaza-dG

<400> SEQUENCE: 3
tctgacgttc t                                                           11

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 4
ctatctcacc ttctctgt                                                    18

<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (7)..(8)
<223> OTHER INFORMATION: 2'-OMe

<400> SEQUENCE: 5
ctatctgacg ttctctgt                                                    18
```

```
<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (11)..(12)
<223> OTHER INFORMATION: 2'-OMe

<400> SEQUENCE: 6
ctatctgacg uuctctgt                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)..(8)
<223> OTHER INFORMATION: 2'-OMe

<400> SEQUENCE: 7
ctatctgacg ttctctgt                                                 18

<210> SEQ ID NO 8
<211> LENGTH: 0
<212> TYPE: DNA
<213> ORGANISM: Artificial Sequence
<220> FEATURE:
<223> OTHER INFORMATION: Synthetic oligonucleotide

<400> SEQUENCE: 8

000

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)..(8)
<223> OTHER INFORMATION: 2'-OMe

<400> SEQUENCE: 9
ctatctgucg ttctctgt                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe

<400> SEQUENCE: 10
ctatctgucg ttctctgt                                                 18

<210> SEQ ID NO 11
```

```
<210> SEQ ID NO 11
<211> LENGTH: 0
<212> TYPE: DNA
<213> ORGANISM: Artificial Sequence
<220> FEATURE:
<223> OTHER INFORMATION: Synthetic oligonucleotide

<400> SEQUENCE: 11

000

<210> SEQ ID NO 12
<211> LENGTH: 0
<212> TYPE: DNA
<213> ORGANISM: Artificial Sequence
<220> FEATURE:
<223> OTHER INFORMATION: Synthetic oligonucleotide

<400> SEQUENCE: 12

000

<210> SEQ ID NO 13
<211> LENGTH: 0
<212> TYPE: DNA
<213> ORGANISM: Artificial Sequence
<220> FEATURE:
<223> OTHER INFORMATION: Synthetic olignucleotide

<400> SEQUENCE: 13

000

<210> SEQ ID NO 14
<211> LENGTH: 0
<212> TYPE: DNA
<213> ORGANISM: Artificial Sequence
<220> FEATURE:
<223> OTHER INFORMATION: Synthetic oligonucleotide

<400> SEQUENCE: 14

000

<210> SEQ ID NO 15
<211> LENGTH: 0
<212> TYPE: DNA
<213> ORGANISM: Artificial Sequence
<220> FEATURE:
<223> OTHER INFORMATION: Synthetic oligonucleotide

<400> SEQUENCE: 15

000

<210> SEQ ID NO 16
<211> LENGTH: 0
<212> TYPE: DNA
<213> ORGANISM: Artificial Sequence
<220> FEATURE:
<223> OTHER INFORMATION: Synthetic oligonucleotide

<400> SEQUENCE: 16

000

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
```

```
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: 7-deaza-dG

<400> SEQUENCE: 17
ctatctgacg ttctctgt                                                 18

<210> SEQ ID NO 18
<211> LENGTH: 0
<212> TYPE: DNA
<213> ORGANISM: Artificial Sequence
<220> FEATURE:
<223> OTHER INFORMATION: Synthetic oligonucleotide

<400> SEQUENCE: 18

000

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: 7-deaza-dG

<400> SEQUENCE: 19
ctatctgucg ttctctgt                                                 18

<210> SEQ ID NO 20
<211> LENGTH: 0
<212> TYPE: DNA
<213> ORGANISM: Artificial Sequence
<220> FEATURE:
<223> OTHER INFORMATION: Synthetic oligonucleotide

<400> SEQUENCE: 20

000

<210> SEQ ID NO 21
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 21
tctgacgttc t                                                        11

<210> SEQ ID NO 22
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(9)
<223> OTHER INFORMATION: P-Me linkage between (8)..(9)
```

```
<400> SEQUENCE: 22
ctatctgacg ttctctgt                                                   18

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(8)
<223> OTHER INFORMATION: P-Me linkage between (7)..(8)

<400> SEQUENCE: 23
ctatctgacg ttctctgt                                                   18

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(9)
<223> OTHER INFORMATION: P-Me linkage between (7)..(8) and (8)..(9)

<400> SEQUENCE: 24
ctatctgacg ttctctgt                                                   18

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)..(9)
<223> OTHER INFORMATION: B-L-deoxy-nucleoside

<400> SEQUENCE: 25
ctatctgacg ttctctgt                                                   18

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: B-L-deoxy-nucleoside

<400> SEQUENCE: 26
ctatctgacg ttctctgt                                                   18

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)..(9)
<223> OTHER INFORMATION: B-L-deoxy-nucleoside
```

```
<400> SEQUENCE: 27
ctatctgtcg ttctctgt                                                    18

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: B-L-deoxy-nucleoside

<400> SEQUENCE: 28
ctatctgtcg ttctctgt                                                    18

<210> SEQ ID NO 29
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)..(9)
<223> OTHER INFORMATION: abasic

<400> SEQUENCE: 29
ctatctgang ttctctgt                                                    18

<210> SEQ ID NO 30
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: abasic

<400> SEQUENCE: 30
ctatctgacn ttctctgt                                                    18

<210> SEQ ID NO 31
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)..(9)
<223> OTHER INFORMATION: abasic

<400> SEQUENCE: 31
ctatctgtng ttctctgt                                                    18

<210> SEQ ID NO 32
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
```

<223> OTHER INFORMATION: abasic

<400> SEQUENCE: 32
ctatctgtcn ttctctgt                                                         18

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)..(9)
<223> OTHER INFORMATION: 3'-deoxy-nucleoside

<400> SEQUENCE: 33
ctatctgacg ttctctgt                                                         18

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: 3'-deoxy-nucleoside

<400> SEQUENCE: 34
ctatctgacg ttctctgt                                                         18

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)..(9)
<223> OTHER INFORMATION: 3'-deoxy-nucleoside

<400> SEQUENCE: 35
ctatctgtcg ttctctgt                                                         18

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: 3'-deoxy-nucleoside

<400> SEQUENCE: 36
ctatctgtcg ttctctgt                                                         18

<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base

```
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: araG

<400> SEQUENCE: 37
ctatctgacg ttctctgt                                                        18

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: araG

<400> SEQUENCE: 38
ctatctgucg ttctctgt                                                        18

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)..(9)
<223> OTHER INFORMATION: araC

<400> SEQUENCE: 39
ctatctgacg ttctctgt                                                        18

<210> SEQ ID NO 40
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)..(9)
<223> OTHER INFORMATION: araC

<400> SEQUENCE: 40
ctatctgucg ttctctgt                                                        18

<210> SEQ ID NO 41
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)..(9)
<223> OTHER INFORMATION: 5-OH-dC

<400> SEQUENCE: 41
ctatctgacg ttctctgt                                                     18

<210> SEQ ID NO 42
<211> LENGTH: 18
<212> TYPE: DNA
<213> ORGANISM: Artificial Sequence
<220> FEATURE:
<223> OTHER INFORMATION: Sythetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)..(9)
<223> OTHER INFORMATION: 5-OH-dC

<400> SEQUENCE: 42
ctatctgucg ttctctgt                                                     18

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)..(9)
<223> OTHER INFORMATION: 1-(2'-deoxy-b-D-ribofuranosyl)-2-oxo-7-deaza-
      8-methyl-purine

<400> SEQUENCE: 43
ctatctgacg ttctctgt                                                     18

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)..(9)
<223> OTHER INFORMATION: 1-(2'-deoxy-b-D-ribofuranosyl)-2-oxo-7-deaza-
      8-methyl-purine

<400> SEQUENCE: 44
ctatctgucg ttctctgt                                                     18

<210> SEQ ID NO 45
<211> LENGTH: 18
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: N1-Me-dG

<400> SEQUENCE: 45
ctatctgacg ttctctgt                                                    18

<210> SEQ ID NO 46
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: N1-Me-dG

<400> SEQUENCE: 46
ctatctgucg ttctctgt                                                    18

<210> SEQ ID NO 47
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)..(9)
<223> OTHER INFORMATION: N3-Me-dC

<400> SEQUENCE: 47
ctatctgacg ttctctgt                                                    18

<210> SEQ ID NO 48
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)..(9)
<223> OTHER INFORMATION: N3-Me-dC

<400> SEQUENCE: 48
ctatctgucg ttctctgt                                                    18

<210> SEQ ID NO 49
<211> LENGTH: 18
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (12)..(12)
<223> OTHER INFORMATION: 3'-OMe

<400> SEQUENCE: 49
ctatctagcg ttctctgt                                                     18

<210> SEQ ID NO 50
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (11)..(11)
<223> OTHER INFORMATION: 3'-OMe

<400> SEQUENCE: 50
ctatctagcg ttctctgt                                                     18

<210> SEQ ID NO 51
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (11)..(12)
<223> OTHER INFORMATION: 3'-OMe

<400> SEQUENCE: 51
ctatctagcg ttctctgt                                                     18

<210> SEQ ID NO 52
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (12)..(12)
<223> OTHER INFORMATION: abasic

<400> SEQUENCE: 52
cctactagcg tnctcatc                                                     18

<210> SEQ ID NO 53
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (11)..(11)
<223> OTHER INFORMATION: abasic

<400> SEQUENCE: 53
cctactagcg ntctcatc                                                     18

<210> SEQ ID NO 54
<211> LENGTH: 18
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)..(8)
<223> OTHER INFORMATION: 3'-deoxy-nucleoside

<400> SEQUENCE: 54
cctactagcg ttctcatc                                                 18

<210> SEQ ID NO 55
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: 3'-OMe

<400> SEQUENCE: 55
tccatgacgt tcctgatgc                                                19

<210> SEQ ID NO 56
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)..(10)
<223> OTHER INFORMATION: B-L-deoxy-nucleoside

<400> SEQUENCE: 56
ctatctgacg ttctctgt                                                 18

<210> SEQ ID NO 57
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(18)
<223> OTHER INFORMATION: B-L-deoxy-nucleoside

<400> SEQUENCE: 57
ctatctgacg ttctctgt                                                 18

<210> SEQ ID NO 58
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(12)
<223> OTHER INFORMATION: C3-linker between (11)..(12)

<400> SEQUENCE: 58
ctatctgacg tctctgt                                                  17

<210> SEQ ID NO 59
```

<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: C3-linker between (10)..(11)

<400> SEQUENCE: 59
ctatctgacg tctctgt                                                  17

<210> SEQ ID NO 60
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: C3-linker-C3-linker between (10)..(11)

<400> SEQUENCE: 60
ctatctgacg ctctgt                                                   16

<210> SEQ ID NO 61
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (12)..(12)
<223> OTHER INFORMATION: abasic

<400> SEQUENCE: 61
ctatctagcg tnctctgt                                                 18

<210> SEQ ID NO 62
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (11)..(11)
<223> OTHER INFORMATION: abasic

<400> SEQUENCE: 62
ctatctagcg ntctctgt                                                 18

<210> SEQ ID NO 63
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (11)..(12)
<223> OTHER INFORMATION: abasic-abasic

<400> SEQUENCE: 63
ctatctagcg nnctctgt                                                 18

```
<210> SEQ ID NO 64
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe

<400> SEQUENCE: 64
ctatctaacg ttctctgt                                                 18

<210> SEQ ID NO 65
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe

<400> SEQUENCE: 65
ctatctagcg ttctctgt                                                 18

<210> SEQ ID NO 66
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe

<400> SEQUENCE: 66
ctatctaucg ttctctgt                                                 18

<210> SEQ ID NO 67
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: 7-deaza-dG

<400> SEQUENCE: 67
ctatctaacg ttctctgt                                                 18

<210> SEQ ID NO 68
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
```

```
<221> NAME/KEY: modified_base
<222> LOCATION: (10)..(10)
<223> OTHER INFORMATION: 7-deaza-dG

<400> SEQUENCE: 68
ctatctagcg ttctctgt                                                    18

<210> SEQ ID NO 69
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: 7-deaza-dG

<400> SEQUENCE: 69
ctatctaucg ttctctgt                                                    18

<210> SEQ ID NO 70
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(12)
<223> OTHER INFORMATION: C3-linker between (11)..(12)

<400> SEQUENCE: 70
ctatctagcg tctctgt                                                     17

<210> SEQ ID NO 71
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: C3-linker between (10)..(11)

<400> SEQUENCE: 71
ctatctagcg tctctgt                                                     17

<210> SEQ ID NO 72
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: C3-linker-C3-linker between (10)..(11)

<400> SEQUENCE: 72
ctatctagcg ctctgt                                                      16

<210> SEQ ID NO 73
<211> LENGTH: 0
```

```
<212> TYPE: DNA
<213> ORGANISM: Artificial Sequence
<220> FEATURE:
<223> OTHER INFORMATION: Synthetic oligonucleotide

<400> SEQUENCE: 73

000

<210> SEQ ID NO 74
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: 2'-OMe

<400> SEQUENCE: 74
ctatctgacg ttctctgt                                                 18

<210> SEQ ID NO 75
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (11)..(12)
<223> OTHER INFORMATION: 2'-OMe

<400> SEQUENCE: 75
ctatctgacg uuctctgt                                                 18

<210> SEQ ID NO 76
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)..(8)
<223> OTHER INFORMATION: N2-Me-dG

<400> SEQUENCE: 76
cctactagcg ttctcatc                                                 18

<210> SEQ ID NO 77
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: 3'-OMe

<400> SEQUENCE: 77
tccatgacgu tcctgatgc                                                19

<210> SEQ ID NO 78
```

-continued

```
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(8)
<223> OTHER INFORMATION: glycerol linker between (7)..(8)

<400> SEQUENCE: 78
ctatctgcgt tctctgt                                                    17

<210> SEQ ID NO 79
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(7)
<223> OTHER INFORMATION: glycerol linker between (6)..(7)

<400> SEQUENCE: 79
ctatctacgt tctctgt                                                    17

<210> SEQ ID NO 80
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: dU

<400> SEQUENCE: 80
ctatctuacg ttctctgt                                                   18

<210> SEQ ID NO 81
<211> LENGTH: 18
<212> TYPE: DNA
<213> ORGANISM: Artificial Sequence
<220> FEATURE:
<223> OTHER INFORMATION: Sythetic oligonucleotide
<220> FEATURE:
<221> NAME/KEY: modified_base
<222> LOCATION: (8)..(8)
<223> OTHER INFORMATION: dU

<400> SEQUENCE: 81
ctatctgucg ttctctgt                                                   18

<210> SEQ ID NO 82
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: glycerol linker between (10)..(11)

<400> SEQUENCE: 82
ctatctgacg tctctgt                                                    17
```

```
<210> SEQ ID NO 83
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(12)
<223> OTHER INFORMATION: glycerol linker between (11)..(12)

<400> SEQUENCE: 83
ctatctgacg tctctgt                                                  17

<210> SEQ ID NO 84
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(8)
<223> OTHER INFORMATION: C3-linker between (7)..(8)

<400> SEQUENCE: 84
ctatctgcgt tctctgt                                                  17

<210> SEQ ID NO 85
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(7)
<223> OTHER INFORMATION: C3-linker between (6)..(7)

<400> SEQUENCE: 85
ctatctacgt tctctgt                                                  17

<210> SEQ ID NO 86
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-OMe

<400> SEQUENCE: 86
tctgacgttc t                                                        11

<210> SEQ ID NO 87
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)..(7)
<223> OTHER INFORMATION: 7-deaza-dG
```

```
<400> SEQUENCE: 87
tctgacgttc t                                                            11

<210> SEQ ID NO 88
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)..(7)
<223> OTHER INFORMATION: araG

<400> SEQUENCE: 88
tctgacgttc t                                                            11

<210> SEQ ID NO 89
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (6)..(7)
<223> OTHER INFORMATION: 2'-OMe

<400> SEQUENCE: 89
tctctgacgt t                                                            11

<210> SEQ ID NO 90
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)..(7)
<223> OTHER INFORMATION: 7-deaza-dG
<220> FEATURE:
<221> NAME/KEY: misc_feature
<222> LOCATION: (11)..(12)
<223> OTHER INFORMATION: C3-linker between (11)..(12)

<400> SEQUENCE: 90
tctgacgttc ttgaccggtc a                                                 21

<210> SEQ ID NO 91
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-OMe

<400> SEQUENCE: 91
tctgucgttc t                                                            11
```

<210> SEQ ID NO 92
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)..(7)
<223> OTHER INFORMATION: 7-deaza-dG

<400> SEQUENCE: 92
tctgucgttc t            11

<210> SEQ ID NO 93
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2-OMe
<220> FEATURE:
<221> NAME/KEY: modified_base
<222> LOCATION: (7)..(7)
<223> OTHER INFORMATION: araG

<400> SEQUENCE: 93
tctgacgttc t            11

<210> SEQ ID NO 94
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)..(7)
<223> OTHER INFORMATION: 7-deaza-dG

<400> SEQUENCE: 94 tctgacgtt            9

<210> SEQ ID NO 95
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)..(7)
<223> OTHER INFORMATION: 7-deaza-dG
<220> FEATURE:
<221> NAME/KEY: misc_feature
<222> LOCATION: (11)..(12)

<223> OTHER INFORMATION: C3-linker between (11)..(12)

<400> SEQUENCE: 95
tctgacgttc ttcaaccaca ca                                           22

<210> SEQ ID NO 96
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (15)..(18)
<223> OTHER INFORMATION: 2'-OMe

<400> SEQUENCE: 96
ctatctgacg ttctcugu                                                18

<210> SEQ ID NO 97
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (15)..(18)
<223> OTHER INFORMATION: 2'-OMe

<400> SEQUENCE: 97
ctatctgucg ttctcugu                                                18

<210> SEQ ID NO 98
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-OMe
<220> FEATURE:
<221> NAME/KEY: modified_base
<222> LOCATION: (5)..(5)
<223> OTHER INFORMATION: 7-deaza-dG

<400> SEQUENCE: 98 ugucgttct                                                           9

<210> SEQ ID NO 99
<211> LENGTH: 9
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-OMe
<220> FEATURE:
<221> NAME/KEY: modified_base
<222> LOCATION: (5)..(5)
<223> OTHER INFORMATION: 7-deaza-dG

<400> SEQUENCE: 99 ugacgttct                                                                    9
```

POTENTIATION OF AUTOIMMUNE AND INFLAMMATORY DISEASE TREATMENTS BY IMMUNE REGULATORY OLIGONUCLEOTIDE (IRO) ANTAGONISTS OF TLR7 AND TLR9

This application claims the benefit of priority from U.S. Provisional Patent Application No. 61/182,928, filed on Jun. 1, 2009, the disclosure of which is explicitly incorporated by reference herein.

BACKGROUND OF THE INVENTION

1. Field of the Invention

The invention generally relates to the field of immunology and immunotherapy, and more specifically to the treatment of autoimmune and inflammatory diseases by competitive inhibitors of tumor necrosis factor alpha.

2. Summary of the Related Art

Inflammation is a complex biological response of the body's tissues to pro-inflammatory agents, such as pathogens. In this response, the body attempts to remove the pro-inflammatory agent while initiating a healing process. In certain diseases that have an inflammatory component (e.g., autoimmune diseases), the body's immune systems respond inappropriately to a non-foreign substance. In this situation, the immune system causes damage to the body's own tissues.

Historically, autoimmune and inflammatory disease have been treated with non-steroidal anti-inflammatory drugs (NSAIDs—such as aspirin, ibuprofen or naproxen), corticosteroids (such as prednisone), anti-malarial medications (such as hydroxychloroquine), or other non-specific medications, including methotrexate, sulfasalazine, leflunomide, cyclophosphamide, and mycophenolate. However, the effectiveness of these treatments is limited.

More recently, competitive inhibitors of tumor necrosis factor alpha (TNF-α) have been developed as more specific treatments for autoimmune and inflammatory disorders. Such competitive inhibitors include etanercept (Embrel®), infliximab (Remicade®), and adalimubab (Humira®). These agents act by binding to TNF-α, thereby making it unavailable to its receptor and preventing it from initiating an inflammatory cascade, and represent a substantial improvement in the treatment of autoimmune and inflammatory disorders.

Such competitive inhibitors of TNF-α have been approved for the treatment of a wide variety of such diseases, including rheumatoid arthritis, arthritis of psoriasis, psoriasis, uveitis, ankylosing spondylitis, Crohn's disease, and sarcoidosis.

Competitive inhibitors of TNF-α have been shown to be useful in other applications as well. Popivanova et al. (2008) *J. Clin. Invest.* 118:560-70, teaches that blocking of TNF-α in mice reduces colorectal carcinogenesis associated with chronic colitis. Fries et al. (2008) *Int. J. Med. Sci.* 5: 169-80, and (2008) *Am. J. Physiol. Gastrointest. Liver Physiol.* 294: G938-G947, respectively, teach that infliximab and etanercept reduce enterocyte apoptosis in experimental colitis in mice and prevented loss of occludin and zonula occludens-1 in enterocyte tight junctions. Coppieters et al. (2006) *Arthritis & Rheumatism* 54:1856-66, teaches that the camelid anti-TNF VHH protein exceeds that of infliximab and adalimumab in a mouse model of rheumatoid arthritis. Zalevsky et al. (2007) *J. Immunol.* 179:1872-83, teaches that dominant-negative inhibitors of TNF attenuate experimental arthritis in a mouse model. Rubbert-Roth and Finckh (2009) *Arthritis Res. Ther.* 11(Suppl 1):S1, reviews the limitations of effectiveness of the FDA approved competitive inhibitors of TNF-α.

In an alternative approach, Newton et al. (2001) *Ann. Rheum. Dis.* 60:iii25-iii32, teaches that inhibitors of TACE, the enzyme that converts pro TNF-α to TNF-α are effective in a mouse model of arthritis.

Unfortunately, all of the currently approved competitive inhibitors of TNF-α have been implicated in the development of severe infections, including tuberculosis, sepsis, and fungal infections. Decreased white and red blood cell and platelet counts and increased incidents of certain cancers have also been associated with treatment with these drugs.

Toll-like receptors (TLRs) are present on many cells of the immune system and have been shown to be involved in the innate immune response (Hornung et al., (2002) *J. Immunol.* 168: 4531-37). In vertebrates, this family consists of ten proteins called TLR1 to TLR10, which are known to recognize pathogen associated molecular patterns from bacteria, fungi, parasites, and viruses (Poltorak et al. (1998) *Science* 282:2085-88; Underhill et al. (1999) *Nature* 401:811-15; Hayashi et al. (2001) *Nature* 410:1099-103; Zhang et al. (2004) *Science* 303:1522-26; Meier et al. (2003) *Cell. Microbiol.* 5:561-70; Campos et al. (2001) *J. Immunol.* 167:416-23; Hoebe et al. (2003) *Nature* 424:743-48; Lund (2003) *J. Exp. Med.* 198:513-20; Heil et al. (2004) *Science* 303:1526-29; Diebold et al. (2004) *Science* 303:1529-31; Hornung et al. (2004) *J. Immunol.* 173:5935-43). TLRs are a key means by which mammals recognize and mount an immune response to foreign molecules and also provide a means by which the innate and adaptive immune responses are linked (Akira et al. (2001) *Nat. Immunol.* 2:675-80; Medzhitov (2001) *Nature Rev. Immunol.* 1:135-45). TLRs have also been shown to play a role in the pathogenesis of many diseases, including autoimmunity, infectious disease, and inflammation (Cook et al. (2004) *Nat. Immunol.* 5:975-79) and the regulation of TLR-mediated activation using appropriate agents may provide a means for disease intervention.

Some TLRs are located on the cell surface to detect and initiate a response to extracellular pathogens and other TLRs are located inside the cell to detect and initiate a response to intracellular pathogens. Table 1 provides a representation of TLRs, the cell types containing the receptor, and the known agonists thereof (Diebold et al. (2004) *Science* 303:1529-31; Liew et al. (2005) *Nature* 5:446-58; Hemmi et al. (2002) *Nat. Immunol.* 3:196-200; Jurk et al. (2002) *Nat. Immunol.* 3:499; Lee et al. (2003) *Proc. Natl. Acad. Sci. U.S.A.* 100:6646-51); (Alexopoulou (2001) *Nature* 413:732-38).

TABLE 1

| TLR Molecule | Agonist | Cell Types Containing Receptor |
|---|---|---|
| Cell Surface TLRs: | | |
| TLR2 | bacterial lipopeptides | Monocytes/macrophages; Myeloid dendritic cells; Mast cells |
| TLR4 | gram negative bacteria | Monocytes/macrophages; Myeloid dendritic cells; Mast cells; Intestinal epithelium |
| TLR5 | motile bacteria | Monocyte/macrophages; Dendritic cells; Intestinal epithelium |
| TLR6 | gram positive bacteria | Monocytes/macrophages; Mast cells; B lymphocytes |

TABLE 1-continued

| TLR Molecule | Agonist | Cell Types Containing Receptor |
|---|---|---|
| Endosomal TLRs: | | |
| TLR3 | double stranded RNA viruses | Dendritic cells; B lymphocytes |
| TLR7 | single stranded RNA viruses; RNA-immunoglobulin complexes | Monocytes/macrophages; Plasmacytoid dendritic cells; B lymphocytes |
| TLR8 | single stranded RNA viruses; RNA-immunoglobulin complexes | Monocytes/macrophages; Dendritic cells; Mast cells |
| TLR9 | DNA containing unmethylated "CpG" motifs; DNA-immunoglobulin complexes | Monocytes/macrophages; Plasmacytoid dendritic cells; B lymphocytes |

Certain unmethylated CpG motifs present in bacterial and synthetic DNA have been shown to activate the immune system and induce antitumor activity. (Tokunaga et al. (1984) *J. Natl. Cancer Inst.* 72:955-62; Shimada et al. (1986) *Jpn. J. Cancer Res.* 77:808-16; Yamamoto et al. (1986) *Jpn. J. Cancer Res.* 79:866-73). Other studies have shown that antisense oligonucleotides containing CpG dinucleotides also stimulate immune responses (Zhao et al. (1996) *Biochem. Pharmacot.* 26:173-82). Subsequent studies demonstrated that TLR9 recognizes unmethylated CpG motifs present in bacterial and synthetic DNA (Hemmi et al. (2000) *Nature* 408: 740-45). Other modifications of CpG-containing phosphorothioate oligonucleotides can also affect their ability to act as modulators of immune response through TLR9 (see, e.g., Zhao et al. (1996) *Biochem. Pharmacol.* 51:173-82; Zhao et al. (1996) *Biochem Pharmacol.* 52:1537-44; Zhao et al. (1997) *Antisense Nucleic Acid Drug Dev.* 7:495-502; Zhao et al. (1999) *Bioorg. Med. Chem. Lett.* 9:3453-58; Zhao et al. (2000) *Bioorg. Med. Chem. Lett.* 10:1051-54; Yu et al. (2000) *Bioorg. Med. Chem. Lett.* 10:2585-88; Yu et al. (2001) *Bioorg. Med. Chem. Lett.* 11:2263-67; and Kandimalla et al. (2001) *Bioorg. Med. Chem.* 9:807-13). In addition, structure activity relationship studies have allowed identification of synthetic motifs and novel DNA-based compounds that induce specific immune response profiles that are distinct from those resulting from unmethylated CpG dinucleotides. (Kandimalla et al. (2005) *Proc. Natl. Acad. Sci. U.S.A.* 102:6925-30; Kandimalla et al. (2003) *Proc. Nat. Acad. Sci. U.S.A.* 100:14303-08; Cong et al. (2003) *Biochem Biophys Res. Commun.* 310: 1133-39; Kandimalla et al. (2003) *Biochem. Biophys. Res. Commun.* 306:948-53; Kandimalla et al. (2003) *Nucleic Acids Res.* 31:2393-400; Yu et al. (2003) *Bioorg. Med. Chem.* 11:459-64; Bhagat et al. (2003) *Biochem. Biophys. Res. Commun.* 300:853-61; Yu et al. (2002) *Nucleic Acids Res.* 30:4460-69; Yu et al. (2002) *J. Med. Chem.* 45:4540-48; Yu et al. (2002) *Biochem. Biophys. Res. Commun.* 297:83-90; Kandimalla et al. (2002) *Bioconjug. Chem.* 13:966-74; Yu et al. (2002) *Nucleic Acids Res.* 30:1613-19; Yu et al. (2001) *Bioorg. Med. Chem.* 9:2803-08; Yu et al. (2001) *Bioorg. Med. Chem. Lett.* 11:2263-67; Kandimalla et al. (2001) *Bioorg. Med. Chem.* 9:807-13; Yu et al. (2000) *Bioorg. Med. Chem. Lett.* 10:2585-88; Putta et al. (2006) *Nucleic Acids Res.* 34:3231-38).

The selective localization of TLRs and the signaling generated therefrom provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g., viral infections, intracellular pathogens, and tumor cells), and results in a secretion of IFN-gamma and a concomitant activation of CTLs. Alternatively, the Th cells involved as helper cells for B-cell activation are Th2 cells. Th2 cells have been shown to be activated in response to bacteria and parasites and may mediate the body's adaptive immune response (e.g., IgE production and eosinophil activation) through the secretion of IL-4 and IL-5. The type of immune response is influenced by the cytokines produced in response to antigen exposure and the differences in the cytokines secreted by Th1 and Th2 cells may be the result of the different biological functions of these two subsets.

As a result of their involvement in regulating an inflammatory response, TLRs have been shown to play a role in the pathogenesis of many diseases, including autoimmunity, infectious disease, and inflammation (Papadimitraki et al. (2007) *J. Autoimmun.* 29: 310-18; Sun et al. (2007) *Inflamm. Allergy Drug Targets* 6:223-35; Diebold (2008) *Adv. Drug Deliv. Rev.* 60:813-23; Cook et al. (2004) *Nat. Immunol.* 5:975-79; Tse and Horner (2008) *Semin. Immunopathol.* 30:53-62; Tobias and Curtiss (2008) *Semin. Immunopathol.* 30:23-27; Ropert et al. (2008) *Semin. Immunopathol.* 30:41-51; Lee et al. (2008) *Semin. Immunopathol.* 30:3-9; Gao et al. (2008) *Semin. Immunopathol.* 30:29-40; Vijay-Kumar et al. (2008) *Semin. Immunopathol.* 30:11-21).

While activation of TLRs is involved in mounting an immune response, an uncontrolled stimulation of the immune system through TLRs may exacerbate certain diseases in immune compromised subjects. Such uncontrolled stimulation may also contribute to autoimmunity or inflammatory disorders.

Thus, there is a need for improved approaches to the treatment of autoimmune and inflammatory diseases.

BRIEF SUMMARY OF THE INVENTION

The invention provides novel immune regulatory oligonucleotides (IRO) compounds as antagonists of TLRs that potentiate the activity of anti-inflammatory agents that act as inhibitors of TNF-α, thereby allowing such inhibitors of TNF-α to be used at lower dosages to mitigate their undesired side effects. These IROs have one or more chemical modifications in the sequence flanking an immune stimulatory motif and/or in an oligonucleotide motif that would be immune stimulatory but for the modification.

Thus, the invention further provides a method for therapeutically treating a mammal having a disease that has an autoimmune or inflammatory component, such method comprising administering to the mammal an IRO compound according to the invention in combination with an inhibitor of TNF-α in a pharmaceutically effective amount. Such diseases include, without limitation, cancer, an autoimmune disorder, airway inflammation, inflammatory disorders, infectious diseases, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma and diseases caused by a pathogen. Preferred autoimmune disorders include without limitation lupus erythematosus, multiple sclerosis, type I diabetes mellitus, irritable bowel syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. Preferred inflammatory disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis, and vasculitis.

The invention further provides a method for preventing the development of a disease or disorder having an autoimmune or inflammatory component comprising administering to a mammal at risk of developing such a disease or disorder an IRO compound according to the invention in combination with an inhibitor of TNF-α in a pharmaceutically effective amount. Such diseases include, without limitation, cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma, and diseases caused by a pathogen in a mammal. Preferred autoimmune disorders include without limitation lupus erythematosus, multiple sclerosis, type I diabetes mellitus, irritable bowl syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia, and Wegener's granulomatosis. Preferred inflammatory disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis, and vasculitis.

The IRO compounds, according to the invention, have the structure 5'-$N_m$—$N_3N_2N_1CGN^1N^2N^3$—$N^m$-3', wherein CG is an oligonucleotide motif and C is cytosine or a pyrimidine nucleotide derivative or non-nucleotide linkage, and G is guanosine or a purine nucleotide derivative or non-nucleotide linkage; $N_1$-$N_3$ and $N^1$-$N^3$, at each occurrence, is independently a nucleotide or nucleotide derivative or non-nucleotide linkage; $N_m$ and $N^m$, at each occurrence, is independently a nucleotide or nucleotide derivative or non-nucleotide linkage; provided that at least one $N_1$ to $N_3$ and/or C and/or G is a nucleotide derivative or non-nucleotide linkage; and further provided that compound contains less than 3 consecutive guanosine nucleotides, wherein the oligonucleotide motif would be immune stimulatory but for the nucleotide derivative or non-nucleotide linkage; and wherein m is a number from 0 to about 30.

In some preferred embodiments, the IRO compound contains less than 4 consecutive guanosine nucleotides.

In some preferred embodiments, the IRO compound is co-administered with one or more inhibitors of TNF-α and one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants, kinase inhibitors, antiviral agents, antimalarial drugs or co-stimulatory molecules, or combinations thereof.

In the several aspects of the invention, the IRO compound is administered in combination with inhibitors of tumor necrosis factor (TNF) activity. TNF is made by the body's immune system, and individuals with immune diseases, for example rheumatoid arthritis, juvenile idiopathic arthritis, ankylosing spondylitis, psoriatic arthritis, and plaque psoriasis, have excessive amounts of TNF in their bodies. As such the co-administration of an IRO with an anti-inflammatory agent that inhibits TNF activity would find use in treating and/or preventing diseases that possess an autoimmune and/or inflammatory component.

Among the embodiments of an anti-inflammatory agent that inhibit TNF that would be useful in combination with an IRO are etanercept (Enbrel®), infliximab (Remicade®), and adalimubab (Humira®). One way the human body protects itself against disease is by increasing blood flow to the affected part of the body. This increased blood flow allows infiltration of immune cells and the production of pro-inflammatory cytokines and chemokines, which results in inflammation. One of the cytokines involved in this inflammatory process is TNF. These inhibitors of TNF bind TNF and help to prevent the pro-inflammatory activity mediated by this molecule Inhibition of this pro-inflammatory activity helps to inhibit inflammatory diseases, including but not limited to rheumatoid arthritis, polyarticular juvenile idiopathic arthritis, psoriatic arthritis, ankylosing spondylitis, and plaque psoriasis.

In some preferred embodiments, the route of administration is parenteral, mucosal delivery, oral, sublingual, transdermal, topical, inhalation, intranasal, aerosol, intraocular, intratracheal, intrarectal, vaginal, by gene gun, dermal patch, or in eye drop or mouthwash form.

DETAILED DESCRIPTION OF THE PREFERRED EMBODIMENTS

Figure 1:
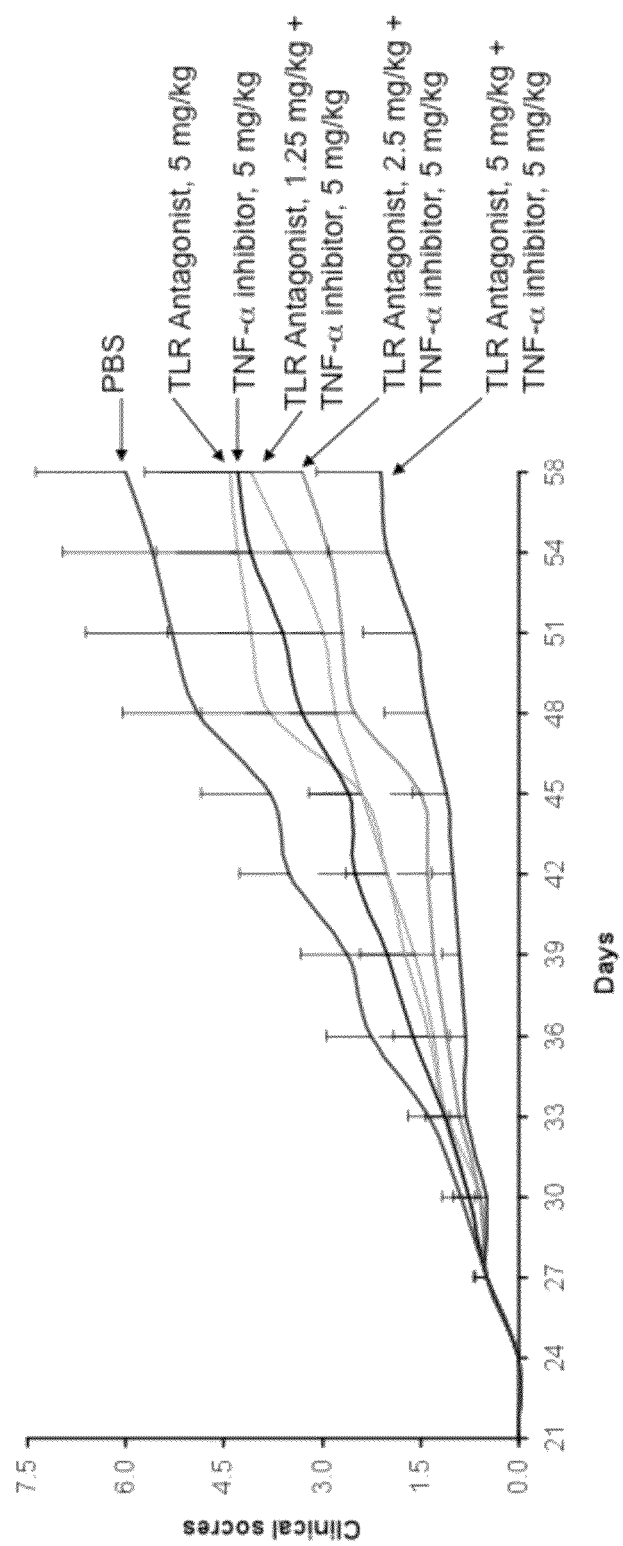
FIG. 1 depicts disease scoring in mice experimentally afflicted with arthritis by intradermal injection of bovine type II collagen/CFA according to Example 2 and illustrates the ability of IRO antagonists of TLR7 and TLR9 to potentiate the activity of an inhibitor of TNF.

The present invention relates to the treatment or prevention of diseases having an autoimmune or inflammatory component. The invention provides novel immune regulatory oligonucleotides (IRO) compounds as antagonists of TLRs that potentiate the activity of anti-inflammatory agents that act as inhibitors of TNF-α, thereby allowing such inhibitors of TNF-α to be used at lower dosages to mitigate their undesired side effects. Specifically, the invention provides Immune Regulatory Oligonucleotide (IRO) compounds as antagonists of toll-like receptors (TLRs) in combination with other anti-inflammatory agents to inhibit and/or suppress selected immune responses. These IROs have unique sequences that inhibit or suppress TLR-mediated signaling in response to endogenous and/or exogenous TLR ligands or agonists. The references cited herein reflect the level of knowledge in the field and are hereby incorporated by reference in their entirety. Any conflicts between the teachings of the cited references and this specification shall be resolved in favor of the latter.

The invention provides methods for suppressing an inappropriate immune response and can be used for immunotherapy applications such as, but not limited to, treatment of cancer, autoimmune disorders, asthma, respiratory allergies, food allergies, skin allergies, systemic lupus erythematosus (SLE), arthritis, pleurisy, chronic infections, inflammatory diseases, inflammatory bowel syndrome, sepsis, and bacteria, parasitic, and viral infections in adult and pediatric human and veterinary applications. Thus, the invention further provides IRO compounds of the invention combined with anti-inflammatory agents that inhibit TNF and that are useful in combination with, for example, DNA vaccines, antigens, antibodies, antiviral agents, antimalarial drugs (for example, chloroquine and hydroxychloroquine), and allergens; and in combination with chemotherapeutic agents (both traditional chemotherapy and modern targeted therapies) and/or antisense oligonucleotides for prevention and treatment of diseases.

The term "oligonucleotide" generally refers to a polynucleoside comprising a plurality of linked nucleoside units. Such oligonucleotides can be obtained from existing nucleic acid sources, including genomic or cDNA, but are preferably produced by synthetic methods. In preferred embodiments each nucleoside unit can encompass various chemical modifications and substitutions as compared to wild-type oligonucleotides, including but not limited to modified nucleoside base and/or modified sugar unit. Examples of chemical modifications are known to the person skilled in the art and are described, for example, in Uhlmann et al. (1990) *Chem. Rev.* 90:543; "Protocols for Oligonucleotides and Analogs" *In Synthesis and Properties & Synthesis and Analytical Techniques* (Agrawal, ed., Humana Press, Totowa, USA, 1993); Hunziker et al. (1995) *Mod. Syn. Methods* 7:331-417; and Crooke et al. (1996) *Ann. Rev. Pharm. Tox.* 36:107-29. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., $(R_P)$- or $(S_P)$-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "2'-substituted ribonucleoside" or "2'-substituted arabinoside" generally includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom or with an aryl group having 6-10 carbon atoms, wherein such hydrocarbyl or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-β-substituted-arabinosides include, without limitation 2'-amino, 2'-fluoro, 2'-allyl, 2'-O-alkyl, and 2'-propargyl ribonucleosides or arabinosides, 2'-O-methylribonucleosides or 2'-β-methylarabinosides, and 2'-O-methoxyethoxyribonucleosides or 2'-β-methoxyethoxyarabinosides.

The term "3'", when used directionally, generally refers to a region or position in a polynucleotide or oligonucleotide 3' (downstream) from another region or position in the same polynucleotide or oligonucleotide.

The term "5'", when used directionally, generally refers to a region or position in a polynucleotide or oligonucleotide 5' (upstream) from another region or position in the same polynucleotide or oligonucleotide.

The term "about" generally means that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above.

The term "adjuvant" generally refers to a substance which, when added to an immunogenic agent such as vaccine or antigen, enhances or potentiates an immune response to the agent in the recipient host upon exposure to the mixture.

The term "agonist" generally refers to a substance that binds to a receptor of a cell and induces a response. Such response may be an increase in the activity mediated by the receptor. An agonist often mimics the action of a naturally occurring substance such as a ligand.

The term "antagonist" or "inhibitor" generally refers to a substance that can bind to a receptor, but does not produce a biological response upon binding. The antagonist or inhibitor can block, inhibit, or attenuate the response mediated by an agonist and may compete with agonist for binding to a receptor. Such antagonist or inhibitory activity may be reversible or irreversible.

The terms "anti-inflammatory agent that inhibits TNF" or "anti-inflammatory agent that inhibits TNF-$\alpha$" generally refers to a substance that has the ability to reduce inflammation by inhibiting the interaction between TNF and its receptor. Examples of such anti-inflammatory agents, include but are not limited to the TNF inhibitors etanercept (Enbrel®), infliximab (Remicade®), and adalimumab (Humira®).

The term "airway inflammation" generally includes, without limitation, asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic immune response upon exposure to the molecule.

The term "allergy" generally refers to an inappropriate immune response characterized by inflammation and includes, without limitation, food allergies and respiratory allergies.

The term "antigen" generally refers to a substance that is recognized and selectively bound by an antibody or by a T-cell antigen receptor, resulting in induction of an immune response. Antigens may include but are not limited to peptides, proteins, nucleosides, nucleotides, and combinations thereof. Antigens may be natural or synthetic, and generally induce an immune response that is specific for that antigen.

The term "antiviral agent" generally refers to an agent that has the capacity to kill viruses, suppress their replication, cell binding or other essential functions and, hence, inhibit their capacity to multiply and reproduce. Such agents may act by stimulating cellular defenses against viruses.

The term "autoimmune disorder" generally refers to disorders in which "self" components undergo attack by the immune system.

The term "TLR-mediated disease" or TLR-mediated disorder" generally means any pathological condition for which activation of one or more TLRs is a contributing factor. Such conditions include but are not limited, cancer, an autoimmune disorder, airway inflammation, inflammatory disorders, infectious disease, skin disorders, allergy, asthma, and diseases caused by a pathogen.

The term "physiologically acceptable" generally refers to a material that does not interfere with the effectiveness of an IRO compound and that is compatible with a biological system such as a cell, cell culture, tissue, or organism. Preferably, the biological system is a living organism, such as a mammal.

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences,* 18th Edition (Gennaro, ed., Mack Publishing Co., Easton, Pa., 1990).

The term "co-administration" generally refers to the administration of at least two different substances sufficiently close in time to modulate an immune response. Co-administration refers to simultaneous administration, as well as temporally spaced order of up to several days apart, of at least two different substances in any order, either in a single dose or separate doses.

The term "complementary" generally means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

The term "disease or disorder having an autoimmune or inflammatory component" means a condition having one or more symptom that results, in whole or in part, from an immune response against a self-antigen or from inflammation.

The term an "effective amount" or a "sufficient amount" generally refers to an amount sufficient to affect a desired biological effect, such as beneficial results. Thus, an "effective amount" or "sufficient amount" will depend upon the context in which it is being administered. In the context of administering a composition that modulates an immune response to a co-administered antigen, an effective amount of an IRO compound and antigen is an amount sufficient to achieve the desired modulation as compared to the immune response obtained when the antigen is administered alone. An effective amount may be administered in one or more administrations.

The term "in combination with" generally means in the course of treating a disease or disorder in a patient, administering an IRO compound and an agent useful for treating the disease or disorder that does not diminish the immune modulatory effect of the IRO compound. Such combination treatment may also include more than a single administration of an IRO compound and/or independently an agent. The administration of the IRO compound and/or the agent may be by the same or different routes.

The term "individual" or "subject" or "mammal" generally refers to but is not limited to, humans, non-human primates, rats, mice, cats, dogs, horses, cattle, cows, pigs, sheep, and rabbits.

The term "kinase inhibitor" generally refers to molecules that antagonize or inhibit phosphorylation-dependent cell signaling and/or growth pathways in a cell. Kinase inhibitors may be naturally occurring or synthetic and include small molecules that have the potential to be administered as oral therapeutics. Kinase inhibitors have the ability to rapidly and specifically inhibit the activation of the target kinase molecules. Protein kinases are attractive drug targets, in part because they regulate a wide variety of signaling and growth pathways and include many different proteins. As such, they have great potential in the treatment of diseases involving kinase signaling, including cancer, cardiovascular disease, inflammatory disorders, diabetes, macular degeneration, and neurological disorders. Examples of kinase inhibitors include sorafenib (Nexavar®), Sutent®, dasatinib, Dasatinib™, Zactima™, Tykerb™, and STI571.

The term "nucleoside" generally refers to compounds consisting of a sugar, usually ribose or deoxyribose, and a purine or pyrimidine base.

The term "nucleotide" generally refers to a nucleoside comprising a phosphate group attached to the sugar.

As used herein, the term "pyrimidine nucleoside" refers to a nucleoside wherein the base component of the nucleoside is a pyrimidine base (e.g., cytosine (C) or thymine (T) or uracil (U)). Similarly, the term "purine nucleoside" refers to a nucleoside wherein the base component of the nucleoside is a purine base (e.g., adenine (A) or guanine (G)).

The terms "analog" or "derivative" can be used interchangeable to generally refer to any purine and/or pyrimidine nucleotide or nucleoside that has a modified base and/or sugar. A modified base is a base that is not guanine, cytosine, adenine, thymine, or uracil. A modified sugar is any sugar that is not ribose or 2' deoxyribose and can be used in the backbone for an oligonucleotide.

The term "inhibiting" or "suppressing" generally refers to a decrease in a response or qualitative difference in a response, which could otherwise arise from eliciting and/or stimulation of a response.

The term "non-nucleotide linker" generally refers to any linkage or moiety that can link or be linked to the oligonucleotides other than through a phosphorous-containing linkage. Preferably such linker is from about 2 angstroms to about 200 angstroms in length.

The term "nucleotide linkage" generally refers to a direct 3'-5' linkage that directly connects the 3' and 5' hydroxyl groups of two nucleosides through a phosphorous-containing linkage.

The term "oligonucleotide motif" generally refers to an oligonucleotide sequence, including a dinucleotide. An "oligonucleotide motif that would be immune stimulatory, but for one or more modifications" means an oligonucleotide motif that is immune stimulatory in a parent oligonucleotide, but not in a derivative oligonucleotide, wherein the derivative oligonucleotide is based upon the parent oligonucleotide, but has one or more modifications that reduce or eliminate immune stimulation.

The terms CpG, C*pG, C*pG*, and CpG* refer to oligonucleotide motifs that are immune stimulatory and comprise cytosine or a cytosine analog and a guanine or a guanine analog.

The term "treatment" generally refers to an approach intended to obtain a beneficial or desired result, which may include alleviation of symptoms, or delaying or ameliorating a disease progression.

In a first aspect, the invention provides an immune regulatory oligonucleotide (IRO) compound. The term "IRO" refers to an immune regulatory oligonucleotide compound that is an antagonist for one or more TLR, wherein the compound comprises an oligonucleotide motif and at least one modification, wherein the oligonucleotide motif would be immune stimulatory (e.g., unmethylated CpG), but for the one or more modifications that suppress the activity of the oligonucleotide motif, provided that the compound contains less than 3 consecutive guanosine nucleotides. Such modifications may be in the oligonucleotide 5' terminus, in a sequence flanking the oligonucleotide motif, and/or within the oligonucleotide motif. These modifications result in an IRO compound that suppresses TLR-modulated immune stimulation. Such modifications can be to the bases, sugar residues, and/or the phosphate backbone of the nucleotides/nucleosides flanking the oligonucleotide motif or within the oligonucleotide motif.

In preferred embodiments, when the modification is a 2' alkylation or alkoxylation then the modification is not 5' adjacent to the oligonucleotide motif when the modification is a non-charged internucleoside linkage then the modification is not 5' adjacent to the oligonucleotide motif; and when the modification is a 3' alkylation or alkoxylation then the modification is not 5' or 3' adjacent to the oligonucleotide motif.

In preferred embodiments the IRO compound is not an antisense oligonucleotide.

The general structure of the IRO compounds may be represented as $5'\text{-}N_m\text{---}N_3N_2N_1CGN^1N^2N^3\text{---}N^{m}\text{-}3'$ wherein CG is an immune stimulatory motif and C is cytosine or a pyrimidine nucleotide derivative or non-nucleotide linker, and G is guanosine or a purine nucleotide derivative or non-nucleotide linker; $N_1\text{-}N_3$ and $N^1\text{-}N^3$, at each occurrence, is independently a nucleotide or nucleotide derivative or non-nucleotide linker; $N_m$ and $N^m$, at each occurrence, is independently a nucleotide or nucleotide derivative or non-nucleotide linker; provided that at least one $N_1$ to $N_3$ and/or C and/or G is a nucleotide derivative or non-nucleotide linker; and further provided that compound contains less than 4 consecutive guanosine nucleotides and preferably less than 3 consecutive guanosines, wherein the immune stimulatory activity of the CG is suppressed by the nucleotide derivative or non-nucleotide linker; and wherein m is a number from 0 to about 30.

In certain embodiments of the invention, IRO compounds may comprise at least two oligonucleotides covalently linked by a nucleotide linkage, or a non-nucleotide linker, at their 5'-, 3'-, or 2'-ends or by functionalized sugar or by functionalized nucleobase via a non-nucleotide linker or a nucleotide linkage. Such IRO compounds may be linear or branched. As a non-limiting example, the linker may be attached to the 3'-hydroxyl. In such embodiments, the linker comprises a functional group, which is attached to the 3'-hydroxyl by means of a phosphate-based linkage like, for example, phosphodiester, phosphorothioate, phosphorodithioate, methylphosphonate, or by non-phosphate-based linkages. Possible sites of conjugation for the ribonucleotide are indicated in Formula I, below, wherein B represents a heterocyclic base and wherein the arrow pointing to P indicates any attachment to phosphorous.

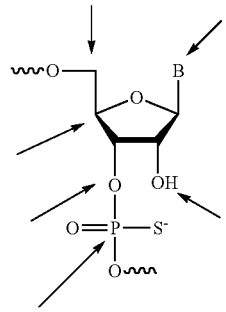

Formula I

In some embodiments, the non-nucleotide linker is a small molecule, macromolecule, or biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligoribonucleotides or appended to it, one or more functional groups including, but not limited to, hydroxy, amino, thiol, thioether, ether, amide, thioamide, ester, urea, or thiourea. The small molecule can be cyclic or acyclic. Examples of small molecule linkers include, but are not limited to, amino acids, carbohydrates, cyclodextrins, adamantane, cholesterol, haptens, and antibiotics. However, for purposes of describing the non-nucleotidic linker, the term "small molecule" is not intended to include a nucleoside.

In some embodiments, the non-nucleotidic linker is an alkyl linker or amino linker. The alkyl linker may be branched or unbranched, cyclic or acyclic, substituted or unsubstituted, saturated or unsaturated, chiral, achiral, or racemic mixture. The alkyl linkers can have from about 2 to about 18 carbon atoms. In some embodiments such alkyl linkers have from about 3 to about 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1,2 propanediol, 1,2,3 propanetriol, 1,3 propanediol, triethylene glycol hexaethylene glycol, polyethylene glycollinkers (e.g., [—O—CH2-CH2-]$_n$ (n=1-9)), methyl linkers, ethyl linkers, propyl linkers, butyl linkers, or hexyl linkers. In some embodiments, such alkyl linkers may include peptides or amino acids.

In some embodiments, the non-nucleotide linker may include, but are not limited to, those listed in Table 2.

TABLE 2

Representative Non-Nucleotidic Linkers

| Non-Nucleotidic Linker No. | Chemical Composition |
|---|---|
| 1 | Glycerol (1,2,3-Propanetriol) |
| 2 | 1,2,4, Butanetriol |
| 3 | 2-(hydroxymethyl)-1,3-propanediol |
| 4 | 2-(hydroxymethyl)1,4-butanediol |
| 5 | 1,3,5-Pentanetriol |
| 6 | 1,1,1-Tris(hydroxymethyl)ethane |
| 7 | 1,1,1-Tris(hydroxymethyl)nitromethane |
| 8 | 1,1,1-Tris(hydroxymethyl)propane |
| 9 | 1,2,6-Hexanetriol |
| 10 | 3-Methyl-1,3,5-pentanetriol |
| 11 | 1,2,6-Methyl-1,3,5-pentanetriol |
| 12 | 1,2,3-Heptanetriol |
| 13 | 2-Amino-2-(hydroxymethyl)-1,3-propanediol |
| 14 | N-[Tris(hydroxymethyl)methyl]acrylamide |
| 15 | cis-1,3,5-Cyclohexanetriol |
| 16 | Cis-1,3,5-Tri(hydroxymethyl)cyclohexane |
| 17 | 1,3,5-Trihydroxyl-benzene |
| 18 | 3,5-Di(hydroxymethyl)phenol |
| 19 | 1,3,5-Di(hydroxymethyl)benzene |
| 20 | 1,3-Di(hydroxyethoxy)-2-hydroxyl-propane |
| 21 | 1,3-Di(hydroxypropoxy)-2-hydroxyl-propane |
| 22 | 2-Deoxy-D-ribose |
| 23 | 1,2,4-Trihydroxyl-benzene |
| 24 | D-Galactoal |
| 25 | 1,6-anhydro-β-D-Glucose |
| 26 | 1,3,5-Tris(2-hydroxyethyl)-Cyanuric acid |
| 27 | Gallic acid |
| 28 | 3,5,7-Trihydroxyflavone |
| 29 | 4,6-Nitropyrogallol |
| 30 | Ethylene glycol |
| 31 | 1,3-Propanediol |
| 32 | 1,2-Propanediol |

TABLE 2-continued

Representative Non-Nucleotidic Linkers

| Non-Nucleotidic Linker No. | Chemical Composition |
|---|---|
| 33 | 1,4-Butanediol |
| 33 | 1,3-Butanediol |
| 34 | 2,3-Butanediol |
| 35 | 1,4-Butanediol |
| 36 | 1,5-Pentanediol |
| 37 | 2,4-Pentanediol |
| 38 | 1,6-Hexanediol |
| 39 | 1,2-Hexanediol |
| 40 | 1,5-Hexanediol |
| 41 | 2,5-Hexanediol |
| 42 | 1,7-Heptanediol |
| 43 | 1,8-Octanediol |
| 44 | 1,2-Octanediol |
| 45 | 1,9-Nonanediol |
| 46 | 1,12-Dodecanediol |
| 47 | Triethylene glycol |
| 48 | Tetraethylene glycol |
| 49 | Hexaethylene glycol |
| 50 | 2-(1-Aminopropyl)-1,3-propanediol |
| 51 | 1,2-Dideoxyribose |

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Some non-nucleotide linkers according to the invention permit attachment of more than two oligonucleotides. For example, the small molecule linker glycerol has three hydroxyl groups to which oligonucleotides may be covalently attached. Some IROs according to the invention, therefore, comprise two or more oligonucleotides linked to a nucleotide or a non-nucleotide linker. Such IROs are referred to as being "branched."

In some embodiments, the IRO compounds may comprise at least two oligonucleotides non-covalently linked, such as by electrostatic interactions, hydrophobic interactions, π-stacking interactions, hydrogen bonding, and combinations thereof. Non-limiting examples of such non-covalent linkage includes Watson-Crick base pairing, Hoogsteen base pairing, and base stacking.

Some of the ways in which two or more oligonucleotides can be linked are shown in Table 3.

TABLE 3

Oligoribonucleotide Formulas IV-XI

| Formula IV | 5' Domain A 3'—X—3' Domain B 5' |
| Formula V | 5' Domain A 3'—X—5' Domain B 3'—X—3' Domain C 5' |
| Formula VI | 5' Domain A 3'—X—5' Domain B 3'—X—5' Domain C 3'—X—3' Domain D 5' |

TABLE 3-continued

Oligoribonucleotide Formulas IV-XI

| Formula VI | 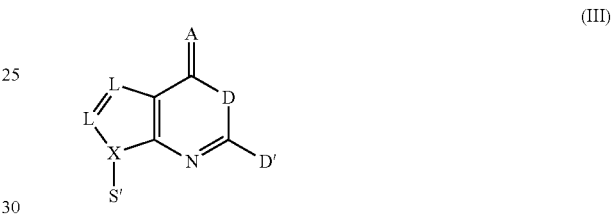 |
| --- | --- |
| Formula VII | 5' Domain A 3'───X───3' Domain B 5' (with sphere below X) |
| Formula IX | 5' Domain A 3'  3' Domain B 5' / X / X / 3' 3' Domain C / 5' Domain D 5' |
| Formula X | 5' Domain A 3' / 3' 5' Domain B / X 3' / Domain C / 5' |
| Formula XI | 3'───5'  5'───3' with X between |

In certain embodiments, pyrimidine nucleosides in the immune regulatory oligonucleotides used in the compositions and methods according to the invention have the structure (II):

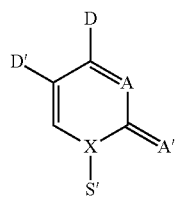

(II)

wherein:
D is a hydrogen bond donor;
D' is selected from the group consisting of hydrogen, hydrogen bond donor, hydrogen bond acceptor, hydrophilic group, hydrophobic group, electron withdrawing group, and electron donating group;
A is a hydrogen bond acceptor or a hydrophilic group;
A' is selected from the group consisting of hydrogen bond acceptor, hydrophilic group, hydrophobic group, electron withdrawing group, and electron donating group;
X is carbon or nitrogen; and
S' is a pentose or hexose sugar ring, or a sugar analog, or a modified sugar.

In certain embodiments, the sugar ring is derivatized with a phosphate moiety, modified phosphate moiety or other linker moiety suitable for linking the pyrimidine nucleoside to another nucleoside or nucleoside analog.

In some embodiments hydrogen bond donors include, without limitation, —NH—, —NH$_2$, —SH, and —OH. Preferred hydrogen bond acceptors include, without limitation, C═O, C═S, and the ring nitrogen atoms of an aromatic heterocycle, e.g., N3 of cytosine.

In some embodiments, (II) is a pyrimidine nucleoside derivative. Examples of pyrimidine nucleoside derivatives include, without limitation, 5-hydroxycytosine, 5-hydroxymethylcytosine, N4-alkylcytosine or N4-ethylcytosine, ara-binoC, 5-OH-dC, N3-Me-dC, and 4-thiouracil. Chemical modified derivatives also include, but are not limited to, thymine or uracil analogues. In some embodiments, the sugar moiety S' in (II) is a sugar derivative. Suitable sugar derivatives include, but are not limited to, trehalose or trehalose derivatives, hexose or hexose derivatives, arabinose or arabinose derivatives.

In some embodiments, the purine nucleosides in immune regulatory oligonucleotides used in the compositions and methods according to the invention have the structure (III):

(III)

(structure diagram)

wherein:
D is a hydrogen bond donor;
D' is selected from the group consisting of hydrogen, hydrogen bond donor, and hydrophilic group;
A is a hydrogen bond acceptor or a hydrophilic group;
X is carbon or nitrogen;
each L is independently selected from the group consisting of C, O, N, and S; and
S' is a pentose or hexose sugar ring, or a sugar analog, or a modified sugar.

In certain embodiments, the sugar ring is derivatized with a phosphate moiety, modified phosphate moiety, or other linker moiety suitable for linking the pyrimidine nucleoside to another nucleoside or nucleoside analog.

In certain embodiments hydrogen bond donors include, without limitation, —NH—, —NH$_2$, —SH, and —OH. In certain embodiments hydrogen bond acceptors include, without limitation, C═O, C═S, —NO$_2$, and the ring nitrogen atoms of an aromatic heterocycle, e.g., N1 of guanine.

In some embodiments, (III) is a purine nucleoside derivative. Examples of purine nucleoside derivatives include, without limitation, guanine analogues such as 7-deaza-G, 7-deaza-dG, ara-G, 6-thio-G, Inosine, Iso-G, Ioxoribine, TOG (7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G (PPG), 2-(Dimethylamino)guanosine, 7-Methyl-6-thioguanosine, 8-Benzyloxyguanosine, 9-Deazaguanosine, 1-(B-D-ribofuranosyl)-2-oxo-7-deaza-8-methyl-purine, or 1-(2'-deoxy-β-D-ribofuranosyl)-2-oxo-7-deaza-8-methyl-purine. Chemically modified derivatives also include, but are not limited to, adenine analogues such as 9-benzyl-8-hydroxy-2-(2-methoxyethoxy)adenine, 2-Amino-N2-O—, methyladenosine, 8-Aza-7-deaza-A, 7-deaza-A, Vidarabine, 2-Aminoadenosine, N1-Methyladenosine, 8-Azaadenosine, 5-Iodotubercidin, and N1-Me-dG. In some embodiments, the sugar moiety S' in (III) is a sugar derivative as defined for Formula II.

In certain embodiments of the invention, the immune regulatory nucleic acid comprises a nucleic acid sequence containing at least one B-L-deoxy nucleoside or 3'-deoxy nucleoside.

In certain embodiments of the invention, the immune regulatory oligonucleotide comprises a nucleic acid sequence containing at least one dinucleotide selected from CpG, C*pG, C*pG*, and CpG*, wherein C is cytosine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2' substituted-arabinoguanosine, 2'-O-substituted-arabinoguanosine, 2'-deoxyinosine, or other purine nucleoside analog, and p is an internucleoside linkage selected from the group consisting of phosphodiester, phosphorothioate, and phosphorodithioate, and wherein the activity of the at least one dinucleotide is regulated by the flanking sequence.

The sequences of specific IROs within these general structures include, but are not limited to, those shown in Table 4a.

TABLE 4a

| IRO/SEQ ID NO: | Sequence |
|---|---|
| 5 | 5'-CTATCT$\underline{GA}$CGTTCTCTGT-3' |
| 7 | 5'-CTATCT$\underline{GA}$CGTTCTCTGT-3' |
| 17 | 5'-CTATCT$\underline{GA}$CG$_1$TTCTCTGT-3' |
| 37 | 5'-CTATCT$\underline{GA}$CG$_4$TTCTCTGT-3' |
| 39 | 5'-CTATCT$\underline{GA}$C$_4$GTTCTCTGT-3' |
| 41 | 5'-CTATCT$\underline{GA}$C$_5$GTTCTCTGT-3' |
| 43 | 5'-CTATCT$\underline{GA}$C$_6$GTTCTCTGT-3' |
| 45 | 5'-CTATCT$\underline{GA}$CG$_5$TTCTCTGT-3' |
| 47 | 5'-CTATCT$\underline{GA}$C$_7$GTTCTCTGT-3' |
| 64 | 5'-CTATCT$\underline{AA}$CGTTCTCTGT-3' |
| 67 | 5'-CTATCT$\underline{AA}$CG$_1$TTCTCTGT-3' |
| 22 | 5'-CTATCTGAmCGTTCTCTGT-3' |
| 9 | 5'-CTATCT$\underline{GU}$CGTTCTCTGT-3' |
| 10 | 5'-CTATCT$\underline{GU}$CGTTCTCTGT-3' |
| 19 | 5'-CTATCT$\underline{GU}$CG$_1$TTCTCTGT-3' |
| 38 | 5'-CTATCT$\underline{GU}$CG$_4$TTCTCTGT-3' |
| 40 | 5'-CTATCT$\underline{GU}$C$_4$GTTCTCTGT-3' |
| 42 | 5'-CTATCT$\underline{GU}$C$_5$GTTCTCTGT-3' |
| 44 | 5'-CTATCT$\underline{GU}$C$_6$GTTCTCTGT-3' |
| 46 | 5'-CTATCT$\underline{GU}$CG$_5$TTCTCTGT-3' |
| 48 | 5'-CTATCT$\underline{GU}$C$_7$GTTCTCTGT-3' |

TABLE 4a-continued

| IRO/SEQ ID NO: | Sequence |
|---|---|
| 66 | 5'-CTATCT$\underline{AU}$CGTTCTCTGT-3' |
| 69 | 5'-CTATCT$\underline{AU}$CG$_1$TTCTCTGT-3' |
| 65 | 5'-CTATCT$\underline{A}$GCGTTCTCTGT-3' |
| 68 | 5'-CTATCT$\underline{A}$GCG$_1$TTCTCTGT-3' |
| 23 | 5'-CTATCTGmACGTTCTCTGT-3' |
| 24 | 5'-CTATCTGmAmCGTTCTCTGT-3' |
| 25 | 5'-CTATCTAC$_2$GTTCTCTGT-3' |
| 27 | 5'-CTATCTGTC$_2$GTTCTCTGT-3' |
| 33 | 5'-CTATCTAC$_3$GTTCTCTGT-3' |
| 35 | 5'-CTATCTGTC$_3$GTTCTCTGT-3' |
| 26 | 5'-CTATCTACG$_2$TTCTCTGT-3' |
| 28 | 5'-CTATCTGTCG$_2$TTCTCTGT-3' |
| 34 | 5'-CTATCTACG$_3$TTCTCTGT-3' |
| 36 | 5'-CTATCTGTCG$_3$TTCTCTGT-3' |
| 21 | 3'-TCTTGCAGTCT-X$_2$-TCTGACGTTCT-3' |
| 52 | 5'-CCTACTAGCGTX$_1$CTCATC-3' |
| 53 | 5'-CCTACTAGCGX$_1$TCTCATC-3' |
| 54 | 5'-CCTACTAG$_3$CGTTCTCATC-3' |
| 55 | 5'-TCCATGA$_1$CGTTCCTGATGC-3' |
| 56 | 5'-CTATCTGAC$_2$G$_2$TTCTCTGT-3' |
| 57 | 5'-C$_2$T$_2$A$_2$T$_2$C$_2$T$_2$G$_2$A$_2$C$_2$G$_2$T$_2$T$_2$C$_2$T$_2$C$_2$T$_2$G$_2$T$_2$-3' |
| 29 | 5'-CTATCTGAX$_1$GTTCTCTGT-3' |
| 30 | 5'-CTATCTGACX$_1$TTCTCTGT-3' |
| 31 | 5'-CTATCTGTX$_1$GTTCTCTGT-3' |
| 32 | 5'-CTATCTGTCX$_1$TTCTCTGT-3' |
| 61 | 5'-CTATCTAGCGTX$_1$CTCTGT-3' |
| 62 | 5'-CTATCTAGCGX$_1$TCTCTGT-3' |
| 63 | 5'-CTATCTAGCGX$_1$X$_1$CTCTGT-3' |
| 58 | 5'-CTATCTGACGTX$_3$CTCTGT-3' |
| 59 | 5'-CTATCTGACGX$_3$TCTCTGT-3' |
| 60 | 5'-CTATCTGACGX$_3$X$_3$CTCTGT-3' |
| 70 | 5'-CTATCTAGCGTX$_3$CTCTGT-3' |
| 71 | 5'-CTATCTAGCGX$_3$TCTCTGT-3' |
| 72 | 5'-CTATCTAGCGX$_3$X$_3$CTCTGT-3' |
| 74 | 5'-CTATCT$\underline{GA}$CGTTCTCTGT-3' |
| 76 | 5'-CCTACTAG$_6$CGTTCTCATC-3' |
| 77 | 5'-TCCATGACGU$_1$TCCTGATGC-3' |
| 78 | 5'-CTATCTGX$_2$CGTTCTCTGT-3' |

TABLE 4a-continued

| IRO/SEQ ID NO: | Sequence |
|---|---|
| 79 | 5'-CTATCTX$_2$ACGTTCTCTGT-3' |
| 80 | 5'-CTATCTU$_2$ACGTTCTCTGT-3' |
| 81 | 5'-CTATCTGU$_2$CGTTCTCTGT-3' |
| 82 | 5'-CTATCTGACGX$_2$TCTCTGT-3' |
| 83 | 5'-CTATCTGACGTX$_2$CTCTGT-3' |
| 84 | 5'-CTATCTGX$_3$CGTTCTCTGT-3' |
| 85 | 5'-CTATCTX3ACGTTCTCTGT-3' |
| 86 | (5'-TCT<u>GA</u>CGTTCT)$_2$X$_2$ |
| 87 | (5'-TCT<u>GA</u>CG$_1$TTCT)$_2$X$_2$ |
| 88 | (5'-TCT<u>GA</u>CG$_4$TTCT)$_2$X$_2$ |
| 89 | (5'-TCTCT<u>GA</u>CGTT)$_2$X$_2$ |
| 90 | 5'-TCT<u>GA</u>CG$_1$TTCT-X$_3$-TGACCGGTCA-3' |
| 91 | (5'-TCT<u>GU</u>CGTTCT)$_2$X$_2$ |
| 92 | (5'-TCT<u>GU</u>CG$_1$TTCT)$_2$X$_2$ |
| 93 | (5'-TCT<u>GA</u>CG$_4$TTCT)$_2$X$_2$ |
| 94 | (5'-TCT<u>GA</u>CG$_1$TT)$_2$X$_2$ |
| 95 | 5'-TCT<u>GA</u>CG$_1$TTCT-X$_3$-TCAACCACACA-3' |
| 96 | 5'-CTATCT<u>GA</u>CG$_1$TTCT<u>CUGU</u>-3' |
| 97 | 5'-CTATCT<u>GU</u>CG$_1$TTCT<u>CUGU</u>-3' |
| 98 | (5'-<u>UGU</u>CG$_1$TTCT)$_2$X$_2$ |
| 99 | (5'-<u>UGA</u>CG$_1$TTCT)$_2$X$_2$ |

Underlined G, A or U=2'-OMe; Underlined T=3'-OMe; A$_1$=3'-OMe; G$_1$=7-deaza-dG; m=P-Me; A$_2$, T$_2$, C$_2$, and G$_2$=B-L-deoxy nucleoside; X$_1$=abasic; X$_2$=glycerol linker, X$_3$=C3-linker; C$_3$ and G$_3$=3'-deoxy-nucleoside; G$_4$=araG; C$_4$=araC; C$_5$=5-OH-dC; G$_6$=N2-Me-dG; C$_6$=1-(2'-deoxy-β-D-ribofuranosyl)-2-oxo-7-deaza-8-methyl-purine; G$_5$=N1-Me-dG; C$_7$=N3-Me-dC; U$_1$=3'-OMe; U$_2$=dU The sequences of control oligonucleotides may include those shown in Table 4b.

TABLE 4b

| SEQ ID NO: | Sequence |
|---|---|
| 1 | 5'-CTATCTGACGTTCTCTGT-3' |
| 2 | 5'-CTATCTGTCGTTCTCTGT-3' |
| 3 | 5'-TCTGACG$_1$TTCT-X$_2$-TCTTG$_1$CAGTCT-5' |
| 4 | 5'-CTATCTCACCTTCTCTGT-5' |
| 6 | 5'-CTATCTGACG<u>UU</u>CTCTGT-3' |
| 49 | 5'-CTATCTAGCGT<u>T</u>CTCTGT-3' |
| 50 | 5'-CTATCTAGCGT<u>T</u>CTCTGT-3' |
| 6 | 5'-CTATCTGACG<u>UU</u>CTCTGT-3' |
| 51 | 5'-CTATCTAGCG<u>TT</u>CTCTGT-3' |
| 75 | 5'-CTATCTGACG$_1$<u>UU</u>CTCTGT-3' |

Underlined U=2'-OMe; Underlined T=3'-OMe; G$_1$=7-deaza-dG; X$_2$=glycerol linker In some embodiments, the oligonucleotides each have from about 6 to about 35 nucleoside residues, preferably from about 9 to about 30 nucleoside residues, and more preferably from about 11 to about 23 nucleoside residues. In some embodiments, the oligonucleotides have from about 6 to about 18 nucleoside residues.

In a second aspect, the invention provides pharmaceutical formulations comprising an IRO compound according to the invention in combination with an anti-inflammatory agent that inhibits TNF and a physiologically acceptable carrier.

In a third aspect, the invention provides methods for inhibiting or suppressing induction of an autoimmune or inflammatory response in a mammal, such methods comprising administering to the mammal an IRO compound according to the invention in combination with an anti-inflammatory agent that inhibits TNF. In preferred embodiments, the IRO compound and the anti-inflammatory agent are administered to a mammal in need of immune suppression.

According to this aspect of the invention, an IRO compound is capable of suppressing an immune response to a further TLR ligand or TLR agonist. The activation of a TLR-based immune response by a TLR agonist or TLR ligand (e.g., an immune modulatory oligonucleotide) can be suppressed/inhibited by the simultaneous, pre- or post-administration of an IRO compound, and such suppression/inhibition may be maintained for an extended period of time (e.g., days) after administration. This beneficial property of the current invention has a unique advantage for the prevention and/or treatment of a disease or disorder. For example, application of certain TLR-agonists in the course of treating the disease may cause unwanted immune stimulation that an IRO compound could suppress/inhibit. Administration of the IRO simultaneously, pre and/or post administration of the TLR-agonist may allow therapeutic benefits from the TLR-agonist while suppressing/inhibiting the unwanted side effect(s). Additionally, pre-administration of an IRO could prevent an immune response (e.g., allergic reaction) to a subsequent or later challenge by a TLR-agonist.

In the methods according to this aspect of the invention, administration of IRO compound in combination with the anti-inflammatory agent that inhibits TNF can be by any suitable route, including, without limitation, parenteral, mucosal delivery, oral, sublingual, transdermal, topical, inhalation, intranasal, aerosol, intraocular, intratracheal, intrarectal, vaginal, by gene gun, dermal patch, or in eye drop or mouthwash form. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of IRO compound from about 0.0001 micromolar to about 10 micromolar. For localized administration, much lower concentrations than this may be effective, and much higher concentrations may be tolerated. Preferably, a total dosage of IRO compound ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

The IRO compound may optionally be linked to one or more allergens and/or antigens (self or foreign), an immunogenic protein, such as keyhole limpet hemocyanin (KLH), cholera toxin B subunit, or any other immunogenic carrier protein. The IRO compound can also be used in combination with other compounds (e.g., adjuvants) including, without limitation, TLR agonists (e.g., TLR2 agonists and TLR9 agonists), Freund's incomplete adjuvant, KLH, monophosphoryl lipid A (MPL), alum, and saponins, including QS-21 and imiquimod, or combinations thereof.

The methods according to this aspect of the invention are useful for model studies of the immune system. The methods are also useful for the prophylactic or therapeutic treatment of human or animal disease. For example, the methods are useful for pediatric and veterinary vaccine applications.

Thus, in a fourth aspect, the invention provides methods for therapeutically treating a patient having a disease or disorder having an autoimmune or inflammatory component, such methods comprising administering to the patient an IRO compound according to the invention in combination with an anti-inflammatory agent that inhibits TNF. In various embodiments, the disease or disorder to be treated is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma, or a disease caused by a pathogen. Pathogens include bacteria, parasites, fungi, viruses, viroids, and prions. Preferred viruses include DNA or RNA viruses such as, but not limited to, double stranded DNA viruses (for example Herpesviruses, Poxviruses, Hepadnaviruses), single-stranded DNA viruses (for example Parvoviruses), single stranded RNA viruses (for example Picornaviruses, Togaviruses, Orthomyanviruses, and Rhabdoviruses), and those listed in Table 5. Administration is carried out as described for in the third aspect of the invention.

TABLE 5

| Virus: | Type: |
|---|---|
| Cytomegalovirus | dsDNA |
| Hepatitis A virus | ssRNA |
| Hepatitis B virus | dsDNA |
| Hepatitis C virus | ssRNA |
| Hepatitis delta virus | ssRNA |
| Hepatitis E virus | ssRNA |
| Herpes simplex virus | dsDNA |
| Human immunodeficiency virus | ssRNA |
| Human papillomavirus | dsDNA |
| Influenzavirus A | ssRNA |
| Influenzavirus B | ssRNA |
| Influenzavirus C | ssRNA |
| Colorado Tick Fever virus | dsRNA |
| Dengue virus | ssRNA |
| Ebolavirus | ssRNA |
| Coxsackie A virus | ssRNA |
| Enterovirus 71 (EV71) | ssRNA |
| Varicella zoster virus | dsDNA |
| Lassa virus | dsDNA |
| Marburg virus | ssRNA |
| Epstein-Barr virus/Human herpesvirus 4 | dsDNA |
| Norovirus | ssRNA |
| Rotavirus | dsRNA |
| JC virus | dsDNA |

TABLE 5-continued

| Virus: | Type: |
|---|---|
| Rabies virus | ssRNA |
| SARS-associated coronavirus | ssRNA |
| Variola virus | dsRNA |
| Human respiratory syncytial virus | ssRNA |
| Adenoviruses | dsDNA |
| Human metapneumovirus | ssRNA |
| West Nile virus | ssRNA |
| Yellow fever virus | ssRNA |
| Picornaviruses | ssRNA |
| Measles virus | ssRNA |
| Mumps virus | ssRNA |
| Poliovirus | ssRNA |
| Rubella virus | ssRNA |
| Japanese encephalitis virus | ssRNA |
| Chandipura virus | ssRNA |
| St. Louis encephalitis virus | ssRNA |
| Eastern equine encephalomyelitis virus | ssRNA |
| Western equine encephalitis virus | ssRNA |
| Venezuelan equine encephalitis virus | ssRNA |

In a fifth aspect, the invention provides methods for preventing a disease or disorder having an autoimmune or inflammatory component, such methods comprising administering to a patient at risk of developing such disease or disorder an IRO compound according to the invention in combination with an anti-inflammatory agent that inhibits TNF. A "patient at risk of developing a disease or disorder" is a patient that has been exposed to an etiologic agent or other environmental factor that causes the disease or disorder, whether or not symptoms of the disease have begun to be manifested. In various embodiments, the disease or disorder to be prevented is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma, or a disease caused by a pathogen. Pathogens include bacteria, parasites, fungi, viruses, viroids, and prions. Preferred viruses include DNA or RNA viruses such as, but not limited to, those listed in Table 5. Administration is carried out as described for the third aspect of the invention.

In any of the methods according to this aspect of the invention, the IRO compound plus the anti-inflammatory agent that inhibits TNF can be administered in combination with any other agent useful for treating the disease or condition that does not diminish the immune modulatory effect of the IRO compound or the anti-inflammatory agent that inhibits TNF. In any of the methods according to the invention, the agent useful for treating the disease or condition includes, but is not limited to, one or more vaccines, antigens, antibodies, cytotoxic agents, allergens, antibiotics, antisense oligonucleotides, TLR agonist, TLR antagonist, peptides, proteins, gene therapy vectors, DNA vaccines, adjuvants, antiviral agents, antimalarial drugs (for example chloroquine and hydroxychloroquine), or kinase inhibitors to enhance the specificity or magnitude of the immune response, or co-stimulatory molecules such as cytokines, chemokines, protein ligands, transactivating factors, peptides, and peptides comprising modified amino acids. For example, in the treatment of cancer, it is contemplated that the IRO compound may be administered in combination with one or more chemotherapeutic compound, targeted therapeutic agent, and/or monoclonal antibody. Alternatively, the agent can include DNA vectors encoding for an antigen or allergen. In these embodiments, the IRO compounds of the invention can variously act as adjuvants and/or produce direct immune modulatory effects.

The following examples are intended to further illustrate certain exemplary embodiments of the invention and are not intended to limit the scope of the invention. For example, representative TLR-ligands are shown in the following examples, but do not limit the scope of ligands to which the IROs of the invention act as antagonists.

Example 1

Synthesis of Oligonucleotides Containing Immune Regulatory Moieties

All IRO were synthesized according to standard procedures (see, e.g., U.S. Patent Publication No. 2004/0097719).

Oligonucleotides were synthesized on a 1 µM scale using an automated DNA synthesizer (Expedite 8909; PerSeptive Biosystems, Framingham, Mass.), following standard linear synthesis or parallel synthesis procedures (see, e.g., FIGS. 5 and 6 of U.S. Patent Publication No. 2004/0097719).

Deoxyribonucleoside phosphoramidites were obtained from (Aldrich-Sigma, St Louis, Mo.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanolphosphoramidite, and methyl phosphonamidite were obtained from Glen Research (Sterling, Va.). β-L-2'-deoxyribonucleoside phosphoramidite, α-2'-deoxyribonucleoside phosphoramidite, mono-DMT-glycerol phosphoramidite, and di-DMT-glycerol phosphoramidite were obtained from ChemGenes (Willmington, Mass.). (4-Aminobutyl)-1,3-propanediol phosphoramidite was obtained from Clontech (Palo Alto, Calif.). Arabinocytidine phosphoramidite, arabinoguanosine, arabinothymidine, and arabinouridine were obtained from Reliable Pharmaceutical (St. Louis, Mo.). Arabinoguanosine phosphoramidite, arabinothymidine phosphoramidite, and arabinouridine phosphoramidite were synthesized at Idera Pharmaceuticals, Inc. (Cambridge, Mass.) (Noronha et al. (2000) *Biochem.* 39:7050-62).

All nucleoside phosphoramidites were characterized by $^{31}$P and $^{1}$H NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2

Antagonists of TLR7 and TLR9 in Combination with Inhibitors of TNF-α Effectively Treat Arthritis Arthritis was induced in DBA/1 mice by intradermal injection (i.d.) of bovine type II collagen (CII)/CFA on day 0 and CII/IFA on day 21.

Mice were divided in to six groups (n=8). Treatment started on day 28 when half of mice in each group displayed arthritis symptoms (score 1). TLR7 and TLR9 antagonist (TLR Antagonist) or Enbrel (TNF-α Inhibitor) or the combination of both agents was administered to mice once in every 3 days up to day 46 (total 7 doses). Mice in Groups 1, 2, and 3 received 1.25, 2.5, and 5 mg/kg of TLR Antagonist by subcutaneous (s.c.) injection, respectively, plus 5 mg/kg TNF-α Inhibitor; mice in Group 4 received 5 mg/kg of TLR Antagonist by subcutaneous (s.c.) injection; mice in Group 5 received 5 mg/kg of TNF-α Inhibitor i.p.; mice in Group 6 received vehicle (PBS) s.c.

Clinical Scores. All mice were monitored for arthritis symptoms every three days from day 21. The arthritis symptoms were scored as 0: no swelling in paws; 1: paws with swelling of at least one digit; 2: paws with swelling of the entire paw; 3: paws with deformity or ankylosis. Each of four paws was scored, with a maximum score of 12 for each mouse. The data are shown in FIG. 1 and demonstrate that the administration of a TLR Antagonist plus a TNF-α Inhibitor agent is more effective at treating and preventing progression of arthritis than either agent alone. More generally, these data demonstrate that the combination of a TLR antagonist plus a TNF-α inhibitor is useful in preventing inflammatory and autoimmune disease progression.

Figure 2:
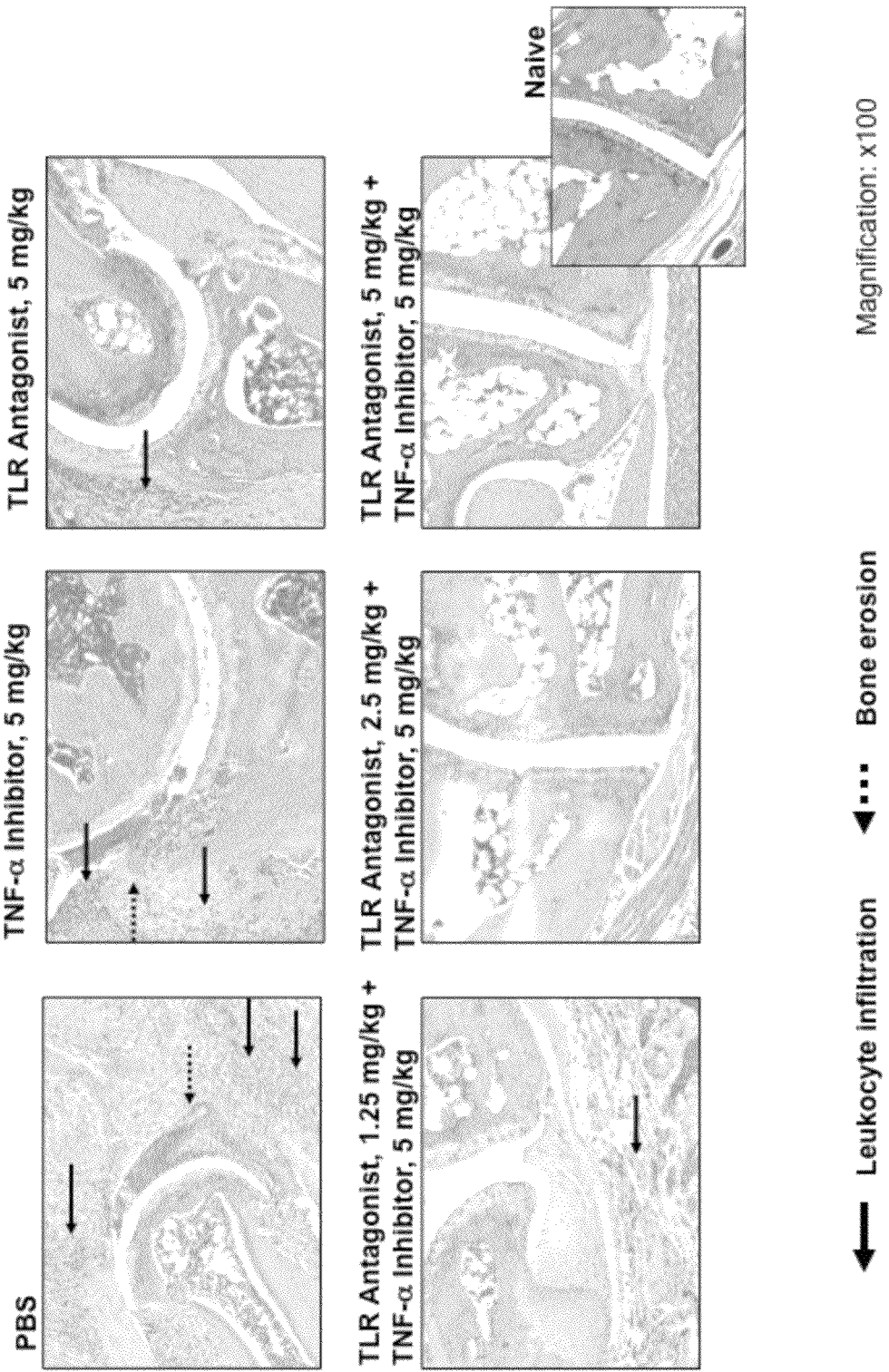
FIG. 2 depicts inflammation and bone erosion in mice experimentally afflicted with arthritis by intradermal injection of bovine type II collagen/CFA according to Example 2 and illustrates the ability of IRO antagonist of TLR7 and TLR9 to enhance or potentiate the anti-inflammatory activity of a TNF inhibitor, resulting in significantly less bone loss in arthritic joints.
Figure 3:
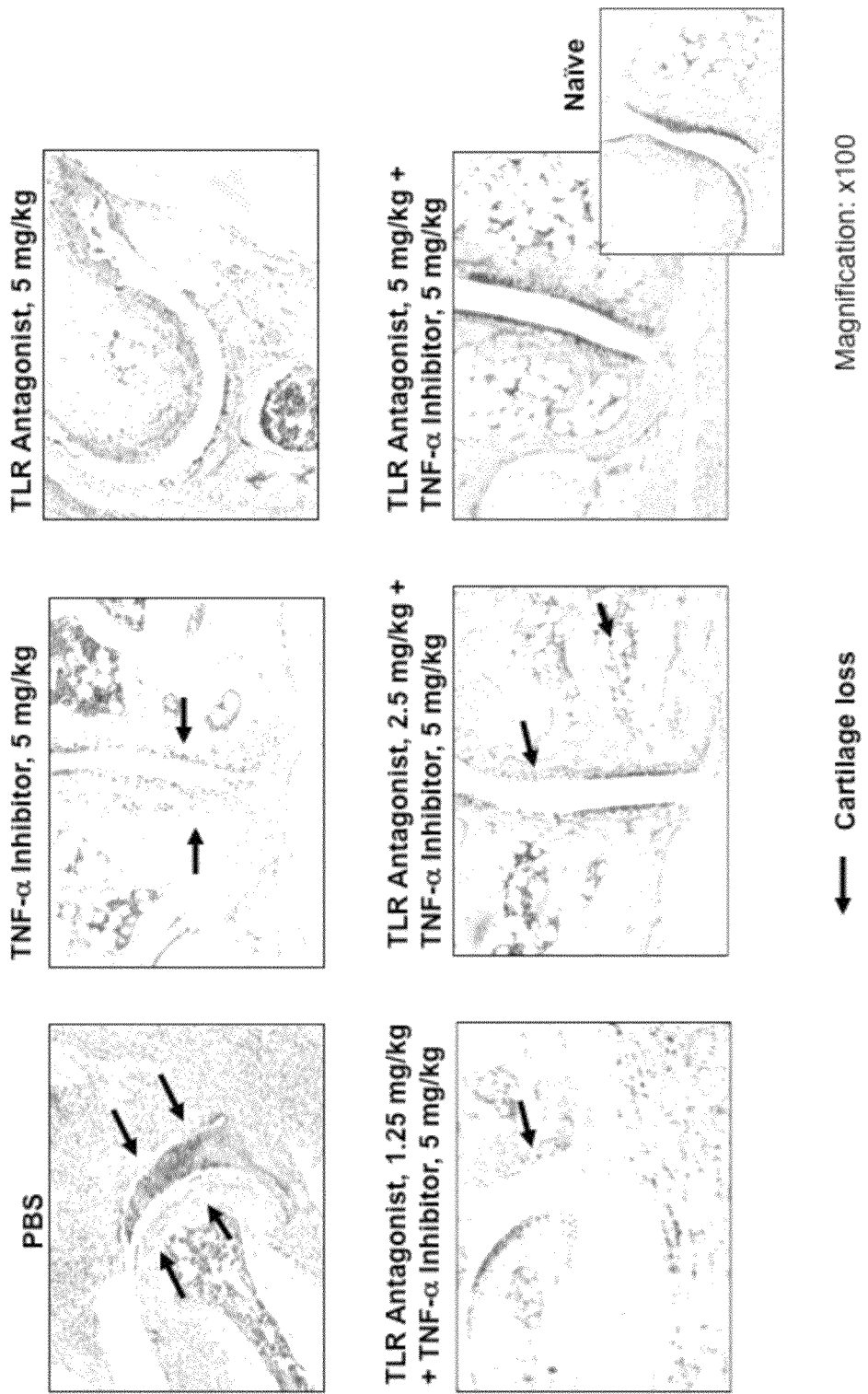
FIG. 3 depicts cartilage loss in mice experimentally afflicted with arthritis by intradermal injection of bovine type II collagen/CFA according to Example 2 and illustrates the ability of IRO antagonist of TLR7 and TLR9 to enhance or potentiate the anti-inflammatory activity of a TNF inhibitor, significantly preserving the cartilage tissue in arthritic joints.

Suppression of Joint Inflammation. At day 58, mice were euthanized and hind foot joint tissues were prepared, fixed, stained with hematoxylin and eosin, and the joint tissue histology evaluated for leukocytes and bone erosion. The data are shown in FIG. 2 and demonstrate that administration of a TLR Antagonist plus a TNF-α Inhibitor is more effective at preventing joint inflammation and the resulting bone erosion than either agent alone. More generally, these data demonstrate that the combination of a TLR antagonist plus a TNF-α inhibitor is useful for inhibiting joint inflammation, bone erosion, and disease progression. Suppression of Cartilage Loss. At day 58, mice were euthanized and hind foot joint tissues were prepared, fixed, stained with Safranin O, and the joint tissue histology evaluated for cartilage loss. The data are shown in FIG. 3 and demonstrate that administration of a TLR Antagonist plus a TNF-α Inhibitor is more effective at preventing cartilage loss than either agent alone. More generally, these data demonstrate that the combination of a TLR antagonist plus a TNF-α inhibitor is useful for inhibiting cartilage loss and disease progression.

Figure 4:
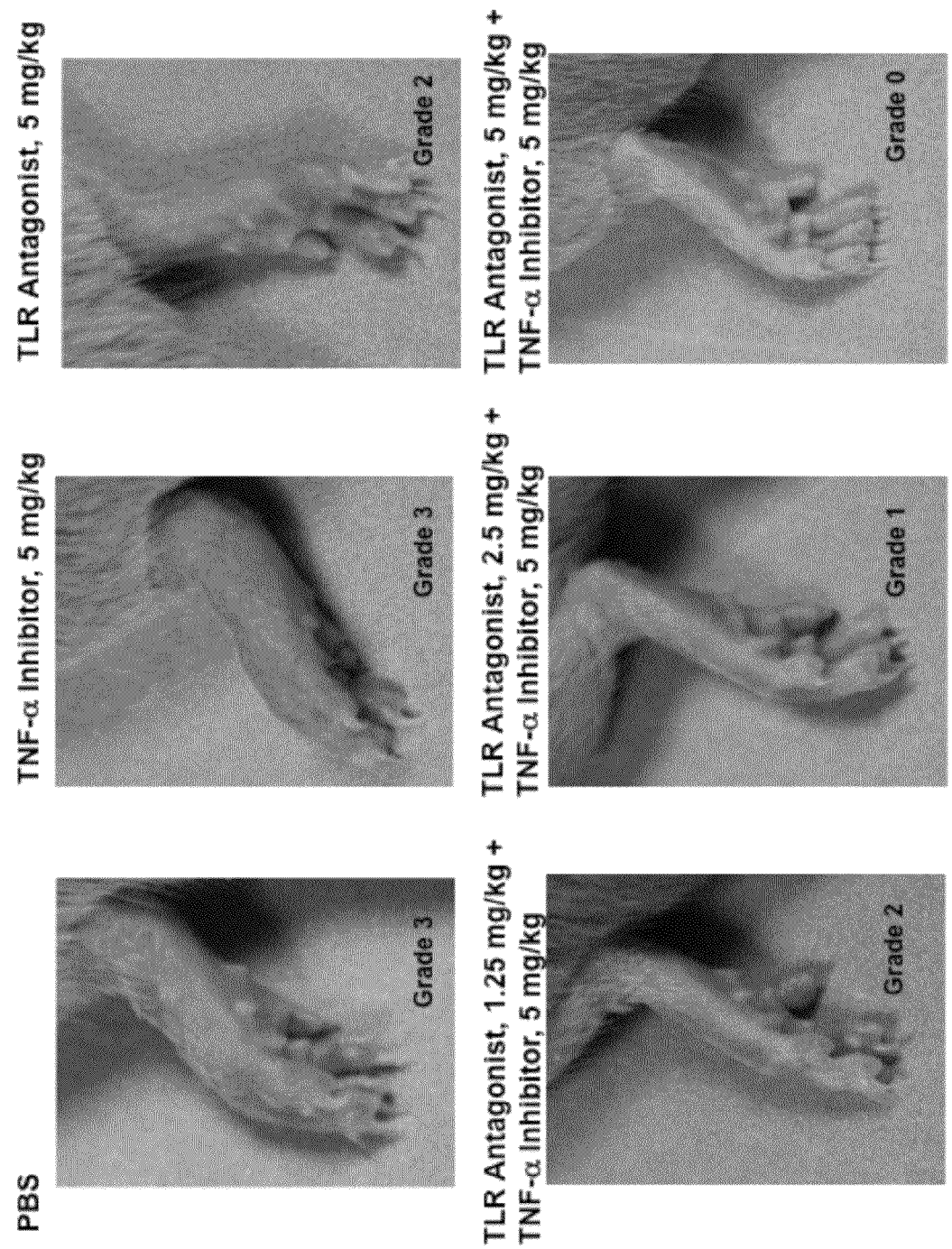
FIG. 4 depicts hind paw swelling in mice experimentally afflicted with arthritis by intradermal injection of bovine type II collagen/CFA according to Example 2 and illustrates the ability of IRO antagonist of TLR7 and TLR9 to enhance or potentiate the anti-inflammatory activity of a TNF inhibitor, resulting in a significant decrease of inflammation on arthritic joints.

Hind Paw Swelling. At day 58, mice were euthanized and hind paws were evaluated and scored for swelling (Grade 0 (no swelling) to Grade 3 (severe swelling)). The data are shown in FIG. 4 and demonstrate that administration of a TLR Antagonist plus a TNF-α Inhibitor is more effective at preventing tissue swelling than either agent alone. More generally, these data demonstrate that the combination of a TLR antagonist plus a TNF-α inhibitor is useful for inhibiting tissue swelling and disease progression.

Figure 5:
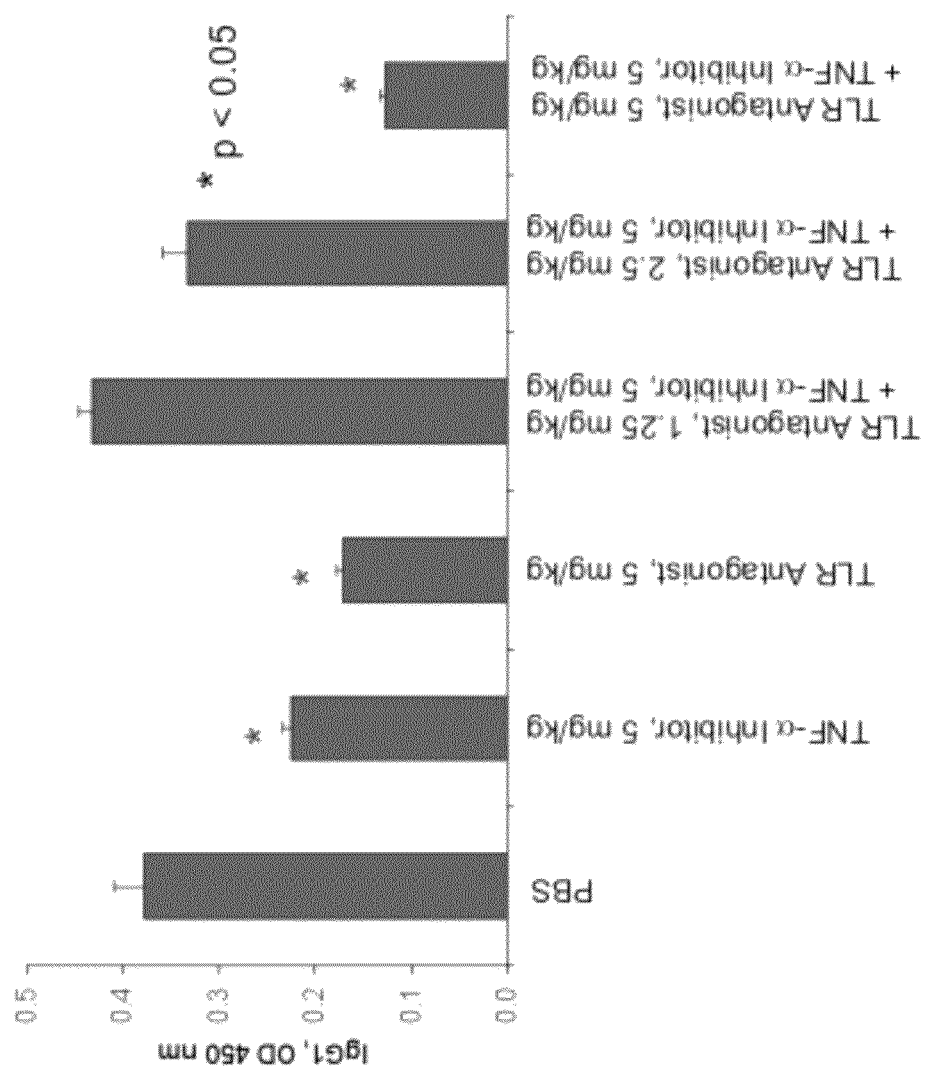
FIG. 5 depicts the Th2 antibody response in mice experimentally afflicted with arthritis by intradermal injection of bovine type II collagen/CFA according to Example 2 and illustrates the ability of IRO antagonist of TLR7 and TLR9 to enhance or potentiate the suppression of a Th2 antibody response by a TNF inhibitor.

IgG1 (Th2 type) Antibody Production. At day 58, mice were euthanized and serum was collected and analyzed for IgG1 (Th2 type) antibody concentration. The data are shown in FIG. 5 and demonstrate that administration of a TLR Antagonist plus a TNF-α Inhibitor effectively inhibits IgG1 antibody production and that the combination of a TLR Antagonist plus a TNF-α Inhibitor is more effective at suppressing IgG1 antibody production than either agent alone. More generally, these data demonstrate that administration of a TLR Antagonist plus a TNF-α inhibitor is useful for inhibiting IgG1 (Th2 type) antibody production and disease progression.

Figure 6:
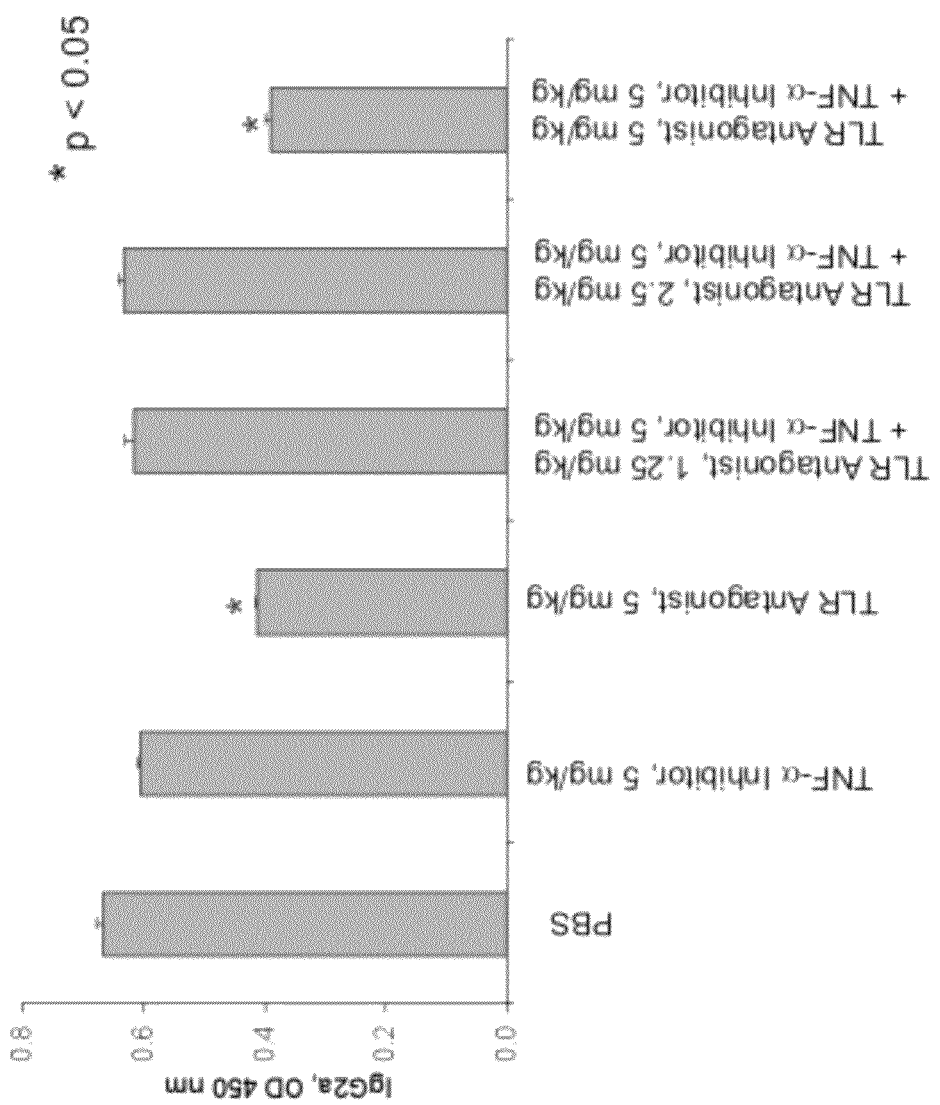
FIG. 6 depicts the Th1 antibody response in mice experimentally afflicted with arthritis by intradermal injection of bovine type II collagen/CFA according to Example 2 and illustrates that TNF inhibitors have limited effect on Th1 antibody response while IRO antagonist of TLR7 and TLR9 have the ability to suppress the Th1 antibody response, even in the presence of a TNF inhibitor.
Figure 7:
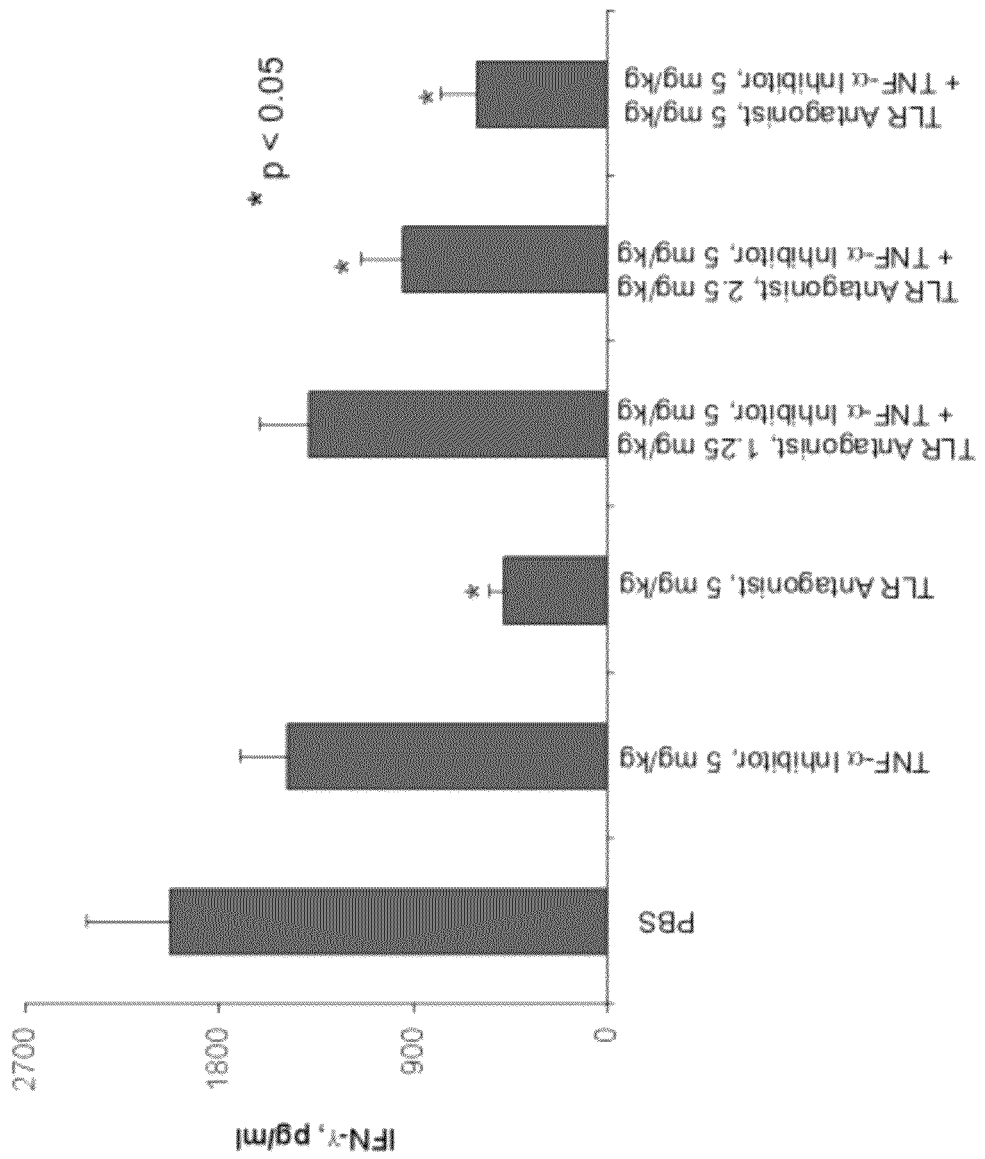
FIG. 7 depicts the Th1 type immune response (e.g., IFN-γ) in mice experimentally afflicted with arthritis by intradermal injection of bovine type II collagen/CFA according to Example 2 and illustrates that TNF inhibitors have limited effect on Th1 immune response while IRO antagonist of TLR7 and TLR9 have the ability to suppress the Th1 antibody response.

IgG2a (Th1 type) Antibody Production. At day 58, mice were euthanized and serum was collected and analyzed for IgG2a (Th1 type) antibody concentration. The data are shown in FIG. 6 and demonstrate that administration of a TLR Antagonist plus a TNF-α Inhibitor effectively inhibits IgG2a (Th1 type) antibody production and that the TLR Antagonist is the agent causing the IgG2a antibody reduction. More generally, these data demonstrate that administration of a TLR Antagonist plus a TNF-α inhibitor is useful for inhibiting IgG2a (Th1 type) antibody production and disease progression.

IFN-γ Production/Immune Response. At day 58, mice were euthanized and serum was collected and analyzed for IFN-γ (Th1 type cytokine) concentration as an indicator of a Th1 type immune response. The data are shown in FIG. 7 and demonstrate that administration of a TLR Antagonist plus a TNF-α Inhibitor effectively inhibits IFN-γ (a Th1 type cytokine) and that the TLR Antagonist is the agent causing the IFN-γ (Th1 type immune response) reduction. More generally, these data demonstrate that administration of a TLR Antagonist plus a TNF-α inhibitor is useful for inhibiting IFN-γ (Th1 type immune response) and disease progression.

What is claimed is:

1. A method for therapeutically treating a mammal having a disease having an autoimmune or inflammatory component where inhibition of tumor necrosis factor alpha (TNF) would be beneficial, such method comprising administering to the mammal an immune regulatory oligonucleotide (IRO) compound in combination with an anti-inflammatory agent that inhibits TNF in a pharmaceutically effective amount wherein the IRO compound comprises an oligonucleotide having the structure $$5'-N_m-N_3N_2N_1CGN^1N^2N^3-N^{m\,l}-3'$$:

wherein:

CG is an oligonucleotide motif that is C*pG, C*pG* or CpG*, wherein C is cytosine, C* is a cytosine nucleotide derivative, G is guanosine and G* is a guanosine nucleotide derivative;

$N_1$ is a modified nucleotide that suppresses the activity of the oligonucleotide motif selected from the group consisting of 2'-substituted ribonucleotide, 2'-O-substituted ribonucleotide, 2'-substituted arabinotide, and 2'-O-substituted arabinotide;

$N_2$-$N_3$, at each occurrence, is independently a nucleotide or nucleotide derivative or a modified nucleotide that suppresses the activity of the oligonucleotide motif selected from the group consisting of 2'-substituted ribonucleotide, 2'-O-substituted ribonucleotide, 2'-substituted arabinotide, and 2'-O-substituted arabinotide; $N^1$—$N^3$, at each occurrence, is independently a nucleotide or nucleotide derivative;

$N_m$ and $N^m$, at each occurrence, is independently a nucleotide or nucleotide derivative or non-nucleotide linkage;

provided that the IRO compound contains less than 3 consecutive guanosine nucleotides;

wherein the oligonucleotide motif would be immune stimulatory but for the one or more modified nucleotides that suppresses the activity of the oligonucleotide motif;

wherein the IRO compound is an antagonist of TLR7, TLR8 and/or TLR9;

wherein the IRO compound is not an antisense oligonucleotide;

wherein the IRO compound potentiates the activity of the anti-inflammatory agent that inhibits TNF;

and wherein m is a number from 0 to about 30.

2. The method according to claim 1, wherein the IRO compound and the anti-inflammatory agent that inhibits TNF are administered in combination with one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants, kinase inhibitors, antiviral agents, or co-stimulatory molecules.

3. The method according to claim 1, wherein the route of administration of the IRO compound and the anti-inflammatory agent that inhibits TNF is independently parenteral, mucosal delivery, oral, sublingual, transdermal, topical, inhalation, intranasal, aerosol, intraocular, intratracheal, intrarectal, vaginal, by gene gun, dermal patch, or in eye drop or mouthwash form.

4. The method according to claim 1, wherein the anti-inflammatory agent that inhibits TNF is etanercept, infliximab, or adalimubab.

5. The method according to claim 1, wherein the disease having an autoimmune or inflammatory component is lupus erythematosus, rheumatoid arthritis, arthritis of psoriasis, psoriasis, uveitis, ankylosing spondylitis, Crohn's disease, sarcoidosis, colitis, or cancer.

6. The method according to claim 1, wherein the IRO compound comprises at least two oligonucleotides linked by a non-nucleotide linker at their 3' ends or by a functionalized sugar or by a functionalized base via a non-nucleotide linker.

7. The method according to claim 6, wherein the non-nucleotide linker linking the at least two oligonucleotides at their 3' ends is Glycerol (1,2,3-Propanetriol), 1,2,4, Butanetriol, 2-(hydroxymethyl)-1,3-propanediol, 2-(hydroxymethyl)1,4-butanediol, 1,3,5-Pentanetriol, 1,1,1-Tris(hydroxymethyl)ethane, 1,1,1-Tris(hydroxymethyl) nitromethane, 1,1,1-Tris(hydroxymethyl)propane, 1,2,6-Hexanetriol, 3-Methyl-1,3,5-pentanetriol, 1,2,3-Heptanetriol, 2-Amino-2-(hydroxymethyl)-1,3-propanediol, N-[Tris(hydroxymethyl)methyl]acrylamide, Cis-1,3,5-Cyclohexanetriol, Cis-1,3,5-Tri(hydroxymethyl)cyclohexane, 3,5-Di(hydroxymethyl)phenol, 1,3,5-Trihydroxyl-benzene, 3,5-Di(hydroxymethyl)benzene, 1,3-Di(hydroxyethoxy)-2-hydroxyl-propane, 1,3-Di(hydroxypropoxy)-2-hydroxyl-propane, 2-Deoxy-D-ribose, 1,2,4-Trihydroxyl-benzene, D-Galactoal, 1,6-anhydro-β-D-Glucose, 1,3,5-Tris(2-hydroxyethyl)-Cyanuric acid, Gallic acid, 3,5,7-Trihydroxyflavone, 4,6-Nitropyrogallol, Ethylene glycol, 1,3-Propanediol, 1,2-Propanediol, 1,4-Butanediol, 1,3-Butanediol, 2,3-Butanediol, 1,4-Butanediol, 1,5-Pentanediol, 2,4-Pentanediol, 1,6-Hexanediol, 1,2-Hexanediol, 1,5-Hexanediol, 2,5-Hexanediol, 1,7-Heptanediol, 1,8-Octanediol, 1,2-Octanediol, 1,9-Nonanediol, 1,12-Dodecanediol, Triethylene glycol, Tetraethylene glycol, 2-(1-Aminopropyl)-1,3-propanediol, or 1,2-Dideoxyribose.

8. The method according to claim 1, wherein the cytosine nucleotide derivative is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other cytosine nucleoside analogs.

9. The method according to claim 1, wherein the guanosine nucleotide derivative is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other guanosine nucleoside analogs.

10. The method according to claim 1, wherein the 2'-O-substituted ribonucleotide is a 2'-OMe-ribonucleotide.

11. The method according to claim 6, wherein the IRO compound is selected from 5'-(TCT$\underline{GA}$CGTTCT)$_2$X$_2$ (5'-SEQ ID NO: 86-3'-X$_2$-3'-SEQ ID NO: 86-5'), 5'-(TCT$\underline{GA}$CG$_1$TTCT)$_2$X$_2$ (5'-SEQ ID NO: 87-3'-X$_2$-3'-SEQ ID NO: 87-5'), 5'-(TCT$\underline{GA}$CG$_4$TTCT)$_2$X$_2$ (5'-SEQ ID NO: 88-3'-X$_2$-3'-SEQ ID NO: 88-5'), 5'-(TCTCT$\underline{GA}$CGTT)$_2$X$_2$ (5'-SEQ ID NO: 89-3'-X$_2$-3'-SEQ ID NO: 89-5'), 5'-(TCT$\underline{GU}$CGTTCT)$_2$X$_2$ (5'-SEQ ID NO: 91-3'-X$_2$-3'-SEQ ID NO: 91-5'), 5'-(TCT$\underline{GU}$CG$_1$TTCT)$_2$X$_2$ (5'-SEQ ID NO: 92-3'-X$_2$-3'-SEQ ID NO: 92-5'), 5'-(TCT$\underline{GA}$CG$_1$TT)$_2$X$_2$ (5'-SEQ ID NO: 94-3'-X$_2$-3'-SEQ ID NO: 94-5'), 5'-($\underline{UG}$UCG$_1$TTCT)$_2$X$_2$ (5'-SEQ ID NO: 98-3'-X$_2$-3'-SEQ ID NO: 98-5') and 5'-($\underline{UG}$ACG$_1$TTCT)$_2$X$_2$ (5'-SEQ ID NO: 99-3'-X$_2$-3'-SEQ ID NO: 99-5'), wherein $G_1$=7-deaza, $G_4$=araG, G, A or U=2'-OMe and $X_2$=glycerol linker.

\* \* \* \* \*

UNITED STATES PATENT AND TRADEMARK OFFICE
CERTIFICATE OF CORRECTION

PATENT NO. : 8,987,221 B2  
APPLICATION NO. : 12/791636  
DATED : March 24, 2015  
INVENTOR(S) : Fu-Gang Zhu et al.

Page 1 of 1

It is certified that error appears in the above-identified patent and that said Letters Patent is hereby corrected as shown below:

In the Claims

Column 67, Claim 1, line 28: please delete the structure "5'-$N_m$-$N_3N_2N_1CGN^1N^2N^3$-$N^{m\ l}$-3':" and replace with -- 5'-$N_m$-$N_3N_2N_1CGN^1N^2N^3$-$N^m$-3': --.

Signed and Sealed this  
Twenty-seventh Day of October, 2015

Michelle K. Lee  
*Director of the United States Patent and Trademark Office*